US009687654B2

(12) United States Patent
Sheldon et al.

(10) Patent No.: US 9,687,654 B2
(45) Date of Patent: *Jun. 27, 2017

(54) SYSTEM AND METHOD FOR DUAL-CHAMBER PACING

(71) Applicant: Medtronic, Inc., Minneapolis, MN (US)

(72) Inventors: Todd J Sheldon, North Oaks, MN (US); James K Carney, Roseville, MN (US); Saul E Greenhut, Aurora, CO (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/694,279

(22) Filed: Apr. 23, 2015

(65) Prior Publication Data
US 2016/0310733 A1 Oct. 27, 2016

(51) Int. Cl.
*A61N 1/00* (2006.01)
*A61N 1/365* (2006.01)
*A61N 1/375* (2006.01)
*A61N 1/362* (2006.01)
(Continued)

(52) U.S. Cl.
CPC .............. *A61N 1/365* (2013.01); *A61N 1/368* (2013.01); *A61N 1/3627* (2013.01); *A61N 1/3684* (2013.01); *A61N 1/3712* (2013.01); *A61N 1/3756* (2013.01)

(58) Field of Classification Search
CPC .... A61N 1/3756; A61N 1/365; A61N 1/3684; A61N 1/3712; A61N 1/36592; A61N 1/36585; A61N 1/3622
See application file for complete search history.

(56) References Cited

U.S. PATENT DOCUMENTS

| 4,967,746 A | 11/1990 | Vandegriff |
| 5,507,782 A | 4/1996 | Kieval et al. |
| 5,683,426 A | 11/1997 | Greenhut et al. |

(Continued)

FOREIGN PATENT DOCUMENTS

| EP | 147820 | 7/1985 |
| EP | 526798 | 2/1993 |

(Continued)

OTHER PUBLICATIONS

Sambelashvili, et al., Coordination of Ventricular Pacing in a Leadless Pacing System, U.S. Appl. No. 14/567,609, filed Dec. 11, 2014, 36pp.

(Continued)

*Primary Examiner* — Robert N Wieland

(57) ABSTRACT

An implantable medical device system including an atrial pacemaker and a ventricular pacemaker is configured to deliver dual chamber pacing in the presence of atrioventricular block. In response to detecting the AV block, the atrial pacemaker may establish a limited number of selectable pacing rates. The atrial pacemaker selects a rate from the limited number of selectable pacing rates and adjusts the atrial pacing rate to the selected rate. The ventricular pacemaker is configured to establish a ventricular pacing rate that is equivalent to the selected rate in response to detecting the AV block. Other examples are described herein.

23 Claims, 11 Drawing Sheets

(51) Int. Cl.
*A61N 1/368* (2006.01)
*A61N 1/37* (2006.01)

(56) References Cited

U.S. PATENT DOCUMENTS

| | | | |
|---|---|---|---|
| 5,683,432 | A | 11/1997 | Goedeke et al. |
| 5,725,561 | A | 3/1998 | Stroebel et al. |
| 5,928,271 | A | 7/1999 | Hess et al. |
| 6,345,201 | B1 | 2/2002 | Sloman et al. |
| 6,920,356 | B2 | 7/2005 | Armstrong et al. |
| 7,031,772 | B2 | 4/2006 | Condie et al. |
| 7,565,195 | B1 | 7/2009 | Kroll et al. |
| 7,630,767 | B1 | 12/2009 | Poore et al. |
| 8,433,409 | B2 | 4/2013 | Johnson et al. |
| 8,532,785 | B1 | 9/2013 | Crutchfield et al. |
| 8,541,131 | B2 | 9/2013 | Lund et al. |
| 8,923,963 | B2 | 12/2014 | Bonner et al. |
| 8,996,109 | B2 * | 3/2015 | Karst ............... A61N 1/36592 607/25 |
| 9,393,424 | B2 | 7/2016 | Demmer et al. |
| 9,399,139 | B2 | 7/2016 | Demmer et al. |
| 2002/0082649 | A1 | 6/2002 | Stahmann et al. |
| 2003/0078627 | A1 | 4/2003 | Casavant et al. |
| 2007/0088405 | A1 | 4/2007 | Jacobson |
| 2007/0293897 | A1 | 12/2007 | Sheldon et al. |
| 2012/0172892 | A1 | 7/2012 | Grubac et al. |
| 2013/0035748 | A1 | 2/2013 | Bonner et al. |
| 2013/0103109 | A1 | 4/2013 | Jacobson |
| 2013/0116738 | A1 | 5/2013 | Samade et al. |
| 2013/0123872 | A1 | 5/2013 | Bornzin et al. |
| 2013/0138006 | A1 | 5/2013 | Bornzin et al. |
| 2014/0121720 | A1 | 5/2014 | Bonner et al. |
| 2014/0323893 | A1 | 10/2014 | Ghosh et al. |
| 2016/0015322 | A1 | 1/2016 | Anderson et al. |

FOREIGN PATENT DOCUMENTS

| | | |
|---|---|---|
| EP | 0559847 | 3/1993 |
| WO | 9216258 | 10/1992 |
| WO | 2006065394 A1 | 6/2006 |
| WO | 2013016374 | 1/2013 |
| WO | 2013096015 | 6/2013 |
| WO | 2014070473 A1 | 5/2014 |

OTHER PUBLICATIONS

Carney et al., Dual Chamber Timing for Leadless Pacemakers Using Infrequent Atrial Signals and Ventricular Contractions, U.S. Appl. No. 14/510,558, filed Oct. 9, 2014, 33pp.

Demmer, et al., System and Method for Dual-Chamber Pacing, U.S. Appl. No. 14/227,962, filed Dec. 22, 2014, 67pp.

(PCT/US2016/025976) PCT Notification of Transmittal of the International Search Report and the Written Opinion of the International Searching Authority, Mailed Aug. 2, 2016, 9 pages.

(PCT/US2015/043904) PCT Notification of Transmittal of the International Search Report and the Written Opinion of the International Searching Authority, mailed Oct. 20, 2015, 11 pages.

(PCT/US2015/042334) PCT Notification of Transmittal of the International Search Report and the Written Opinion of the International Searching Authority, mailed Oct. 21, 2015, 10 pages.

\* cited by examiner

SYSTEM AND METHOD FOR DUAL-CHAMBER PACING

TECHNICAL FIELD

The disclosure relates to an implantable medical device system and associated method for controlling intracardiac pacemakers to deliver coordinated dual chamber pacing to a patient's heart.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are wholly implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular pacing may adequately address some patient conditions, other conditions may require atrial and ventricular pacing, commonly referred to as dual chamber pacing, in order to maintain a regular heart rhythm.

SUMMARY

In general, the disclosure is directed to implantable medical device (IMD) systems including an atrial pacemaker and a ventricular pacemaker configured to deliver coordinated dual chamber pacing during AV block without requiring communication between the two pacemakers on a beat-by-beat basis. A pacemaker operating according to the techniques disclosed herein establishes a limited selection of pacing rates in response to detecting atrioventricular (AV) block. The limited pacing rate selection has fewer pacing rates available to select for pacing a heart chamber than the pacing rates that are available when AV block is not detected.

In one example, the disclosure provides a method comprising selecting a first chamber pacing rate from a first plurality of selectable pacing rates, automatically detecting AV block, and, in response to detecting the AV block, establishing a second plurality of selectable pacing rates comprising fewer selectable pacing rates than the first plurality of selectable pacing rates. The method further includes selecting a first rate from the second plurality of selectable pacing rates, adjusting the first chamber pacing rate to the first rate, delivering first pacing pulses to a first heart chamber at the selected first rate; establishing a second chamber pacing rate that is equivalent to the first rate in response to detecting the AV block; and delivering second pacing pulses to a second heart chamber at the established second chamber rate.

In another example, the disclosure provides an implantable medical device (IMD) system comprising a first chamber pacemaker comprising a first pacing pulse generator, a first sensing module and a first control module coupled to the first pacing pulse generator and the first sensing module and a second chamber pacemaker comprising a second pacing pulse generator, a second sensing module, and a second control module coupled to the second pulse generator and the second sensing module. The first chamber pacemaker is configured to select a first chamber pacing rate from a first plurality of selectable pacing rates, detect AV block, and, in response to detecting the AV block, establish a second plurality of selectable pacing rates comprising fewer selectable rates than the first plurality of selectable pacing rates. The first control module is further configured to select a rate from the second plurality of selectable pacing rates, adjust the first pacing rate to the selected rate, and control the first pulse generator to deliver first pacing pulses to a first heart chamber at the selected rate. The second control module is configured to detect the AV block, establish a second chamber pacing rate that is equivalent to the first rate in response to detecting the AV block; and control the second pacing pulse generator to deliver second pacing pulses to a second heart chamber at the established second chamber pacing rate.

In yet another example, the disclosure provides a non-transitory, computer-readable storage medium comprising a set of instructions which, when executed by an implantable medical device system comprising a first chamber pacemaker and a second chamber pacemaker, cause the system to select a first chamber pacing rate from a first plurality of selectable pacing rates, detect atrioventricular (AV) block, in response to detecting the AV block, establish a second plurality of selectable pacing rates comprising fewer selectable pacing rates than the first plurality of selectable pacing rates, select a rate from the second plurality of selectable pacing rates, adjust the first chamber pacing rate to the selected rate, deliver pacing pulses to a first heart chamber at the selected rate, establish a second chamber pacing rate that is equivalent to the selected rate in response to detecting the AV block, and deliver second chamber pacing pulses to a second heart chamber at the established second chamber pacing rate.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below

DETAILED DESCRIPTION

An implantable medical device (IMD) system is disclosed herein that includes an atrial intracardiac pacemaker and a ventricular intracardiac pacemaker that do not require transvenous leads but are enabled to provide coordinated atrial and ventricular pacing without wired communication signals between the two intracardiac pacemakers. Each of the atrial and ventricular intracardiac pacemakers are configured to select a pacing rate during AV block that results in coordinated, sequential AV pacing without requiring communication signals between the two pacemakers on a continuous beat-to-beat basis.

In past practice, a dual chamber pacemaker positioned in an implant pocket and coupled to transvenous atrial and ventricular leads may be programmed to deliver only atrial pacing (e.g., AAI(R)), only ventricular pacing (e.g., VVI(R)) or both (e.g., DDD(R)) according to patient need. The dual chamber pacemaker is able to control the delivery of pacing pulses in both atrial and ventricular chambers because the pacemaker will receive cardiac event signals from both the atrial and ventricular chambers via correspondingly placed sensing electrodes and control when a pacing pulse is delivered in both chambers relative to the sensed events using the electrodes positioned in both chambers. In other words, the dual chamber pacemaker "knows" when both sensed and paced events occur in both atrial and ventricular pacing channels since all sensing and pacing control is happening in the one device, i.e., the dual chamber pacemaker.

An intracardiac pacemaker can operate in a single chamber mode, e.g., AAI or VVI, by delivering pacing pulses and inhibiting pacing when an intrinsic event is sensed in the chamber that the pacemaker is implanted in. While some patients may require only single chamber pacing and sensing, patients having AV conduction defects may require a pacing system capable of delivering coordinated dual chamber pacing to provide pacing in the ventricle that is properly timed relative to atrial pacing pulses or sensed P-waves. A dual chamber pacing system and associated techniques are disclosed herein which provide coordinated atrial and ventricular pacing during periods of AV block.

Figure 1:
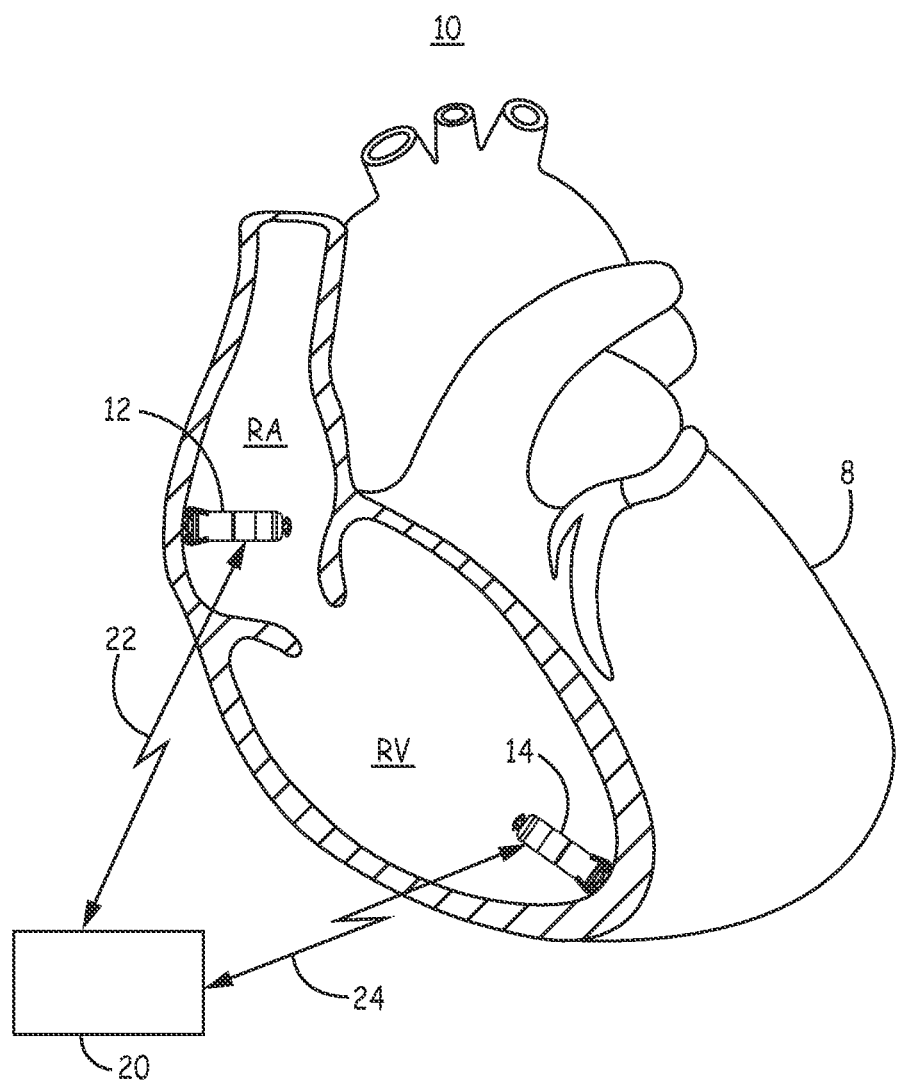
FIG. 1 is a conceptual diagram illustrating an intracardiac pacing system that may be used to sense cardiac electrical signals and provide therapy to a patient's heart.

FIG. 1 is a conceptual diagram illustrating an intracardiac pacing system 10 that may be used to sense cardiac electrical signals and provide therapy to a patient's heart 8. IMD system 10 includes a right atrial (RA) intracardiac pacemaker 12 and a right ventricular (RV) intracardiac pacemaker 14. Pacemakers 12 and 14 are transcatheter intracardiac pacemakers adapted for implantation wholly within a heart chamber, e.g., wholly within the RV, wholly within the left ventricle (LV), wholly within the RA or wholly within the left atrium (LA) of heart 8. In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex. The techniques disclosed herein, however, are not limited to the pacemaker locations shown in the example of FIG. 1 and other positions and relative locations from each other are possible. In some examples, a RA intracardiac pacemaker 12 and a LV intracardiac pacemaker are implanted for delivering coordinated atrial and ventricular pacing using the techniques disclosed herein.

Pacemakers 12 and 14 are reduced in size compared to a typical subcutaneously implanted pacemaker and may be generally cylindrical in shape to enable transvenous implantation via a delivery catheter. In other examples, pacemakers 12 and 14 may be positioned at any other location inside or outside heart 8, including epicardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, i.e., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using one or more housing based electrodes and deliver RV pacing pulses.

The RA pacemaker 12 and the RV pacemaker 14 are configured to control the delivery of pacing pulses to the respective atrial and ventricular chambers in a manner that promotes maintaining a target AV delay between atrial pacing pulses and ventricular pacing pulses during AV block. A target AV delay may be a programmed value selected by a clinician. A target AV delay may be identified as being hemodynamically optimal for a given patient based on clinical testing or assessments or based on automated analysis of electrical activity or hemodynamic function using implanted sensors.

Pacemakers 12 and 14 may each capable of bidirectional wireless communication with an external device 20. External device 20 may be a programmer used by a clinician or other user in a medical facility, a home monitor located in a patient's home, or a handheld device. Aspects of external device 20 may generally correspond to the external programming/monitoring unit disclosed in U.S. Pat. No. 5,507,782 (Kieval, et al.), hereby incorporated herein by reference in its entirety.

External device 20 may be configured to establish a wireless radio frequency (RF) communication link 22 with RA pacemaker 12 and wireless RF communication link 24 with RV pacemaker 14 using a communication protocol that appropriately addresses the targeted pacemaker 12 or 14. An example RF telemetry communication system that may be implemented in system 10 is generally disclosed in U.S. Pat. No. 5,683,432 (Goedeke, et al.), hereby incorporated herein by reference in its entirety.

External device 20 may be used for retrieving data from pacemakers 12 and 14 and for sending data to pacemakers 12 and 14. Examples of retrieved data include physiological signals such as RA or RV EGM signals, therapy delivery data such as a history of pacing frequency, results of device diagnostic testing, current operating control parameters or other data stored by the pacemaker. Data sent to pacemakers 12 and 14 may include programmable control parameters used by the pacemakers 12 and 14 to control sensing and pacing functions, including AV delay and minimum and maximum pacing rates.

RA pacemaker 12 and RV pacemaker 14 may or may not be configured to communicate directly with each other. For example, neither RA pacemaker 12 nor RV pacemaker 14 may be configured to initiate an RF communication session with the other device. Both pacemakers 12, 14 may be configured to periodically "listen" for a valid "wake up" telemetry signal from external device 20 and power up its own telemetry module to establish a communication link 22 or 24 in response to a valid RF telemetry signal (or go back to "sleep" if no valid telemetry signal is received). However, pacemakers 12 and 14 may not be configured to transmit a "wake up" signal to the other pacemaker to initiate a communication session. In other examples, the pacemakers 12 and 14 may be configured to communicate with each other, but, in order to conserve battery life of the intracardiac pacemakers, telemetry communication may be minimized. As such, communication does not occur on a continuous beat-by-beat basis between the RA pacemaker 12 and RV pacemaker 14 for communicating when the other pacemaker is sensing cardiac events or when it is delivering pacing pulses.

Figure 2A:
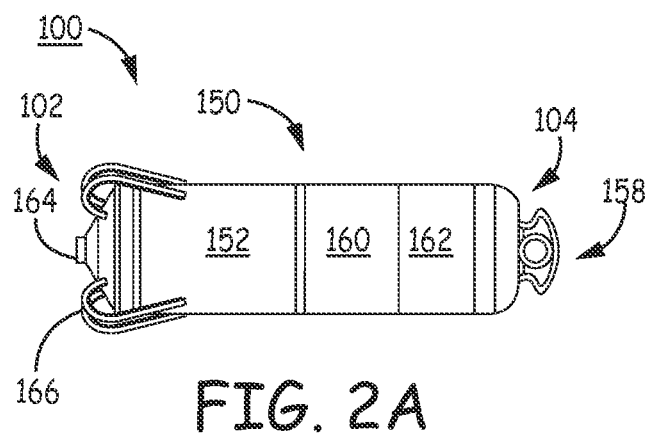
FIG. 2A is a conceptual diagram of an intracardiac pacemaker that may correspond to the atrial pacemaker or the ventricular pacemaker shown in FIG. 1.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. Relatively greater inter-electrode spacing will increase the likelihood of sensing far field (FF) signals that may be used by the pacemaker 100 for sensing events in another heart chamber. For example, an increased inter-electrode spacing between electrodes 162 and 164 when pacemaker 100 is used as an RV pacemaker 14 may improve reliable sensing of FF atrial pacing pulses. Increased spacing between electrodes 162 and 164 may improve reliable sensing of FF R-waves by RA pacemaker 12. FF sensing may be used for detecting AV block and/or adjusting the relative phase of AA and VV pacing intervals during AV block to achieve a desired AV delay between an atrial pacing pulse and a ventricular pacing pulse.

In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as a return sensing electrode, isolated from tip electrode 164, instead of providing a localized electrode such as electrode 162.

The housing 150 includes a control electronics subassembly 152, which houses the electronics for sensing cardiac signals, producing pacing pulses and controlling therapy delivery and other functions of pacemaker 100. Tip electrode 164 may be coupled via an electrical feedthrough to a pacing pulse generator included in control electronics subassembly to function as the pacing cathode. Ring electrode 162 may be coupled to the housing 150 to serve as the return anode.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae or atrial pectinate muscles. Fixation tines 166 are configured to anchor pacemaker 100 to position electrode 164 in operative proximity to a targeted tissue for delivering therapeutic electrical stimulation pulses. Pacemaker 100 may include a set of active fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 is located at the proximal end 104 of pacemaker 100 and is configured to connect to a delivery device, such as a catheter, used to position pacemaker 100 at an implant location during an implantation procedure, for example within a heart chamber. The reduced size of pacemaker 100 enables implantation wholly within a heart chamber.

Figure 2B:
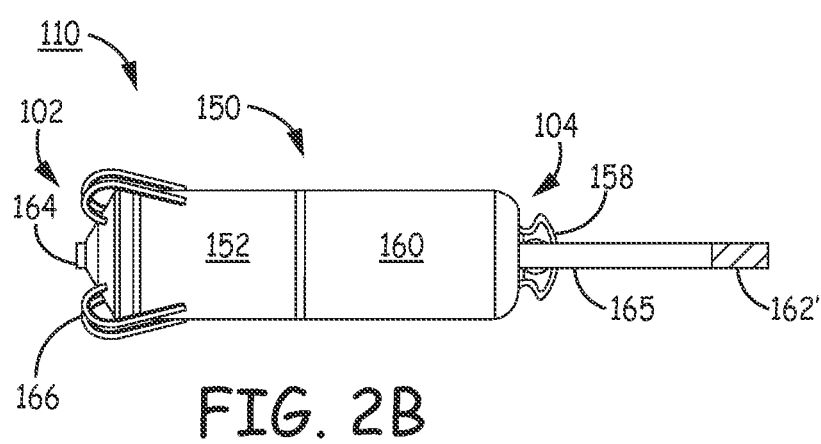
FIGS. 2B and 2C are conceptual diagrams of alternative examples of intracardiac pacemakers that may be included in the system of FIG. 1.
Figure 2C:
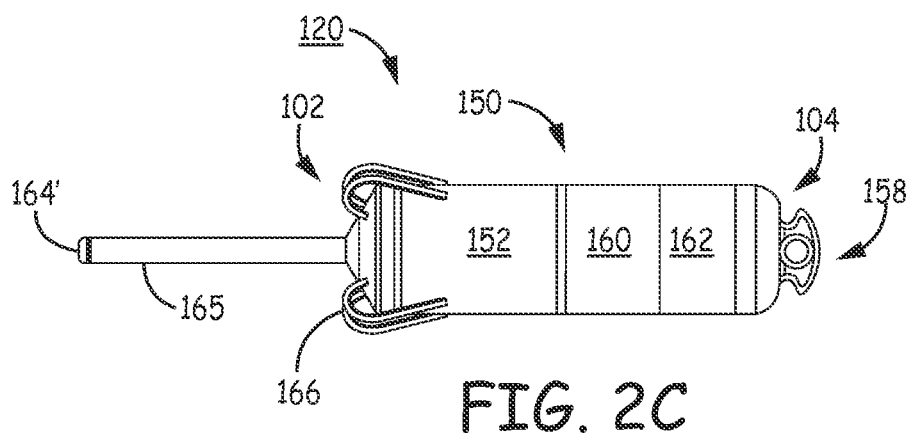

FIGS. 2B and 2C are conceptual diagrams of alternative examples of a pacemaker 110 and pacemaker 120, respectively. In other examples, as shown by pacemaker 110 of FIG. 2B, a proximal sensing extension 165 may carry the return anode electrode 162', which may be electrically coupled to the housing 150, for positioning the return anode electrode at an increased inter-electrode distance from distal tip electrode 164. In still other examples, as shown in FIG. 2C, pacemaker 120 may include a distal extension 168 carrying distal cathode electrode 164 electrically coupled to control electronics assembly 152. Reference is made to commonly-assigned U.S. Publication No. 2013/0035748 (Bonner, et al.) and U.S. Patent Application Ser. No. 62/025,690, filed on Jul. 17, 2014, both of which references are incorporated herein by reference their entirety.

Figure 3:
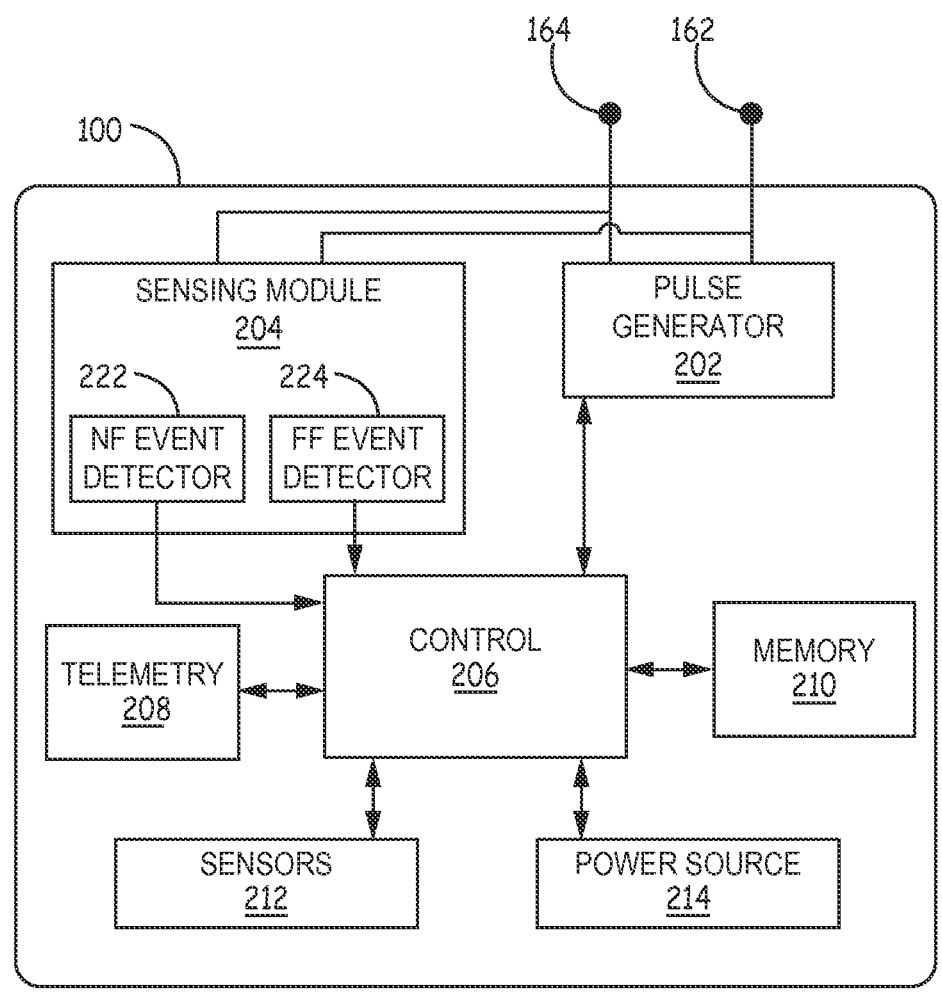
FIG. 3 is a functional block diagram of an example configuration of the pacemaker shown in FIG. 2A.

FIG. 3 is a functional block diagram of an example configuration of pacemaker 100. Pacemaker 100 includes a pulse generator 202, a sensing module 204, a control module 206, memory 210, telemetry module 208 and a power source 214. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Each of RA pacemaker 12 and RV pacemaker 14 will include similar modules as represented by the pacemaker 100 shown in FIG. 3; however it is understood that the modules are configured differently as needed to perform the functionality of the separate RA and RV pacemakers 12 and 14 as disclosed herein.

For example, when pacemaker 100 is configured as RA pacemaker 12, control module 206 is configured to set various atrial pacing escape intervals used to control delivery of atrial pacing pulses as disclosed herein. When pacemaker 100 is embodied as RV pacemaker 14, control module 206 is configured to set ventricular pacing escape intervals to control delivery of RV pacing pulses according to techniques disclosed herein. Adaptations of the hardware, firmware or software of the various modules of pacemaker 100 necessary to meet the described functionality of the intracardiac pacemakers 12 and 14 positioned in different heart chambers as disclosed herein is understood to be included in the various modules of pacemaker 100 according to the intended implant location.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in associated memory 210 and relying on input from sensing module 204.

Pulse generator 202 generates electrical stimulation pulses that are delivered to heart tissue via electrodes 162 and 164. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, e.g., as controlled by a pacing escape interval timer included in a pace timing and control circuit in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing escape interval according to programmed therapy control parameters stored in memory 210. The pace timing and control circuit included in control module 206 includes an escape interval timer or counter that is set to various pacing escape intervals used for controlling the timing of pacing pulses relative to a paced or sensed event. Upon expiration of a pacing escape interval, a pacing pulse is delivered. If a cardiac event is sensed during the pacing timing interval by sensing module 204, the scheduled pacing pulse may be inhibited. Control of pacing escape intervals by control module 206 are described below in conjunction with the various flow charts and timing diagrams presented herein.

Sensing module 204 includes cardiac event detectors 222 and 224 for receiving cardiac EGM signals developed across electrodes 162 and 164. A cardiac event is sensed by sensing module 204 when the EGM signal crosses a sensing threshold of a cardiac event detector 222 or 224 in some examples. The sensing threshold may be an auto-adjusting sensing threshold that may be initially set based on the amplitude of a sensed event and decays at a predetermined decay rate thereafter. In response to a sensing threshold crossing, sensing module 204 passes a sensed event signal to control module 206.

Sensing module 204 may include a near-field (NF) event detector 222 and a far-field (FF) event detector 224. NF cardiac events are events that occur in the heart chamber where the electrodes 162 and 164 are located. FF cardiac events are events that occur in a different heart chamber than the heart chamber where electrodes 162 and 164 are located.

The NF cardiac event detector 222 of RA pacemaker 12 may be programmed or configured to operate using a sensing threshold appropriate for sensing P-waves attendant to the depolarization of the atria. The NF cardiac event detector 222 of RV pacemaker 14 may be programmed or configured to operate using a sensing threshold appropriate for sensing R-waves attendant to the depolarization of the ventricles. NF cardiac event detector 222 produces a sensed event signal provided to control module 206 in response to sensing a NF event, i.e., a P-wave by RA pacemaker 12 or an R-wave by RV pacemaker 14.

The terms "sensed cardiac events" or "sensed events" as used herein refer to events sensed by sensing module 204 in response to the EGM signal crossing a sensing threshold, which may be an amplitude threshold, a frequency threshold, a slew rate threshold, or any combination thereof. NF sensed events are intrinsic events arising in the heart in the absence of a pacing pulse delivered in the heart chamber in which the intrinsic event is sensed. Intrinsic events include intrinsic P-waves, such as sinus P-waves originating from the sino-atrial node of the heart, and intrinsic R-waves, such as sinus R-waves conducted through the heart's normal conduction pathway to the ventricles from the atria via the atrioventricular node. Intrinsic events can also include non-sinus intrinsic events, such as premature atrial contractions (PACs) or premature ventricular contractions (PVCs) that arise intrinsically from the heart (i.e., not due to a pacing pulse) but are ectopic in origin.

FF event detector 224 may be configured to sense FF ventricular events when pacemaker 100 is embodied as RA pacemaker 12. A FF ventricular event sensing threshold may be used by FF event detector 224 for sensing FF ventricular events (also referred to herein as "FFV events"). FF event detector 224 produces a FF sensed event signal that is passed to control module 206 in response to sensing a FFV event. FF ventricular events sensed by FF event detector 224 in RA pacemaker 12 may include ventricular pacing pulses delivered by RV pacemaker 14 and/or R-waves, intrinsic or evoked.

In RV pacemaker 14, a FF event detector 224 may be configured to sense FF atrial pacing pulses. The inter-electrode spacing of sensing electrodes 162 and 164 may be increased to enhance sensing of small amplitude FF atrial pacing pulses by FF event detector 224, e.g., by using a sensing extension as shown in FIG. 2B.

When available, FF atrial pace (FFAP) event signals produced by FF event detector 224 in RV pacemaker 14 may be used by control module 206 of RV pacemaker 14 to adjust the ventricular pacing escape interval, also referred to herein as a "VV pace interval," to match an atrial paced rate and maintain a phase of the VV pace interval relative to an atrial pacing escape interval ("AA pace interval") at a desired AV delay according to techniques disclosed herein. As described below, RV pacemaker 14 may monitor for AV conduction block and adjust the ventricular pacing rate to match an atrial pacing rate selected from a limited number of pacing rates. This rate adjustment may be performed by control module 206 of RV pacemaker 14 based on FFAP event signals received from FF event detector 224.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals, counters, or other data used by control module 206 to control the delivery of pacing pulses by pulse generator 202, e.g., by setting a pacing escape interval timer included in control module 206, according to the techniques disclosed herein.

Pacemaker 100 may further include one or more physiological sensors 212 used for monitoring the patient. In some examples, physiological sensors 212 include at least one physiological sensor producing a signal indicative of the metabolic demand of the patient. The signal indicative of the patient's metabolic demand is used by control module 206 for determining a sensor indicated pacing rate to control the pacing rate to meet the patient's metabolic demand. For example, sensors 212 may include an accelerometer for producing a patient activity signal passed to control module 206. The accelerometer can be referred to as a rate response sensor because it produces a signal correlated to patient body motion, which is indicative of metabolic demand, enabling rate responsive pacing.

If rate responsive pacing is enabled, the accelerometer signal is used by the control module 206 to determine a sensor-indicated rate (SIR) used to establish a temporary lower rate pacing interval. The control module 206 sets the pacing escape interval based on the established lower rate interval for controlling the pacing rate to meet the metabolic demand of the patient. RA pacemaker 12 may initially set the atrial pacing escape interval timer included in control module 206 to a lower rate interval corresponding to a programmed base pacing rate to provide bradycardia pacing, e.g., at 60 pulses per minute (ppm). The lower rate interval may be shortened from the base lower rate interval automatically to provide atrial rate responsive pacing according to the sensor indicated rate determined from the rate response sensor signal, e.g., a patient activity signal from an accelerometer included in sensors 212. The use of a patient activity signal for providing rate-responsive pacing is generally disclosed in U.S. Pat. No. 7,031,772 (Condie, et al.), incorporated herein by reference in its entirety.

When AV conduction is intact, the RA pacemaker 12 and the RV pacemaker 14 operate in an AV conduction mode in which the ventricular rate will naturally follow the rate-responsive atrial pacing rate. The RA pacemaker 12 senses near-field intrinsic P-waves by NF detector 222. A scheduled atrial pacing pulse is inhibited by control module 206 of RA pacemaker 12 if a P-wave is sensed during an AA pace interval and is delivered if the AA pace interval expires without sensing a P-wave. The RA pacemaker 12 may adjust the AA pace interval as needed according to the SIR across a full range of available pacing rate selections. The RV pacemaker 14 provides backup ventricular pacing by setting a relatively long VV pace interval to allow naturally conducted depolarizations to take place. As long as ventricular R-waves are sensed by NF event detector 222 of RV pacemaker 14, ventricular pacing pulses are inhibited.

If AV block is detected by the RA pacemaker 12 and/or the RV pacemaker 14 during the AV conduction mode, as described in greater detail below, the RA pacemaker 12 and the RV pacemaker 14 enter an AV block pacing mode. In the AV block pacing mode, RA pacemaker 12 selects an atrial pacing rate from a limited number of pacing rates. The selected pacing rate may be based on the intrinsic atrial rate or a SIR and is selected to provide pacing control of the atrial rate (at a rate greater than the intrinsic atrial rate as long as the intrinsic atrial activity is not tachyarrhythmic). The RV pacemaker 14 is configured to select a ventricular pacing rate to be equal to the atrial pacing rate. The RV pacemaker control module 206 may select the ventricular pacing rate based on a SIR and/or based on FF atrial pace event signals produced by FF event detector 224.

A physiological signal produced by sensors 212 may additionally or alternatively be used by sensing module 204 and/or control module 206 to detect mechanical activity of the patient's heart, such as pressure or motion of a heart chamber or heart sounds. For example, a mechanical heart signal may be used for detecting AV block based on an absence of a ventricular heart sound, pressure signal, or other mechanical signal indicative of ventricular systole.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data via a radio frequency (RF) communication link. RF communication with external device 20 (FIG. 1), may occur in the Medical Implant Communication Service (MICS) band, the Medical Data Service (MEDS) band, or other frequency bands, including, but not limited to a 2.4 GHz industrial, scientific and medical (ISM) band for Bluetooth and IEEE 802.11 b/g/n standards. Telemetry module 208 may be capable of bi-directional communication with external device 20 over a wide range of distances, e.g., up to approximately 10 meters. In other examples, telemetry communication may require the use of a programming head placed in proximity of pacemaker 100 to facilitate data transfer.

Figure 4A:
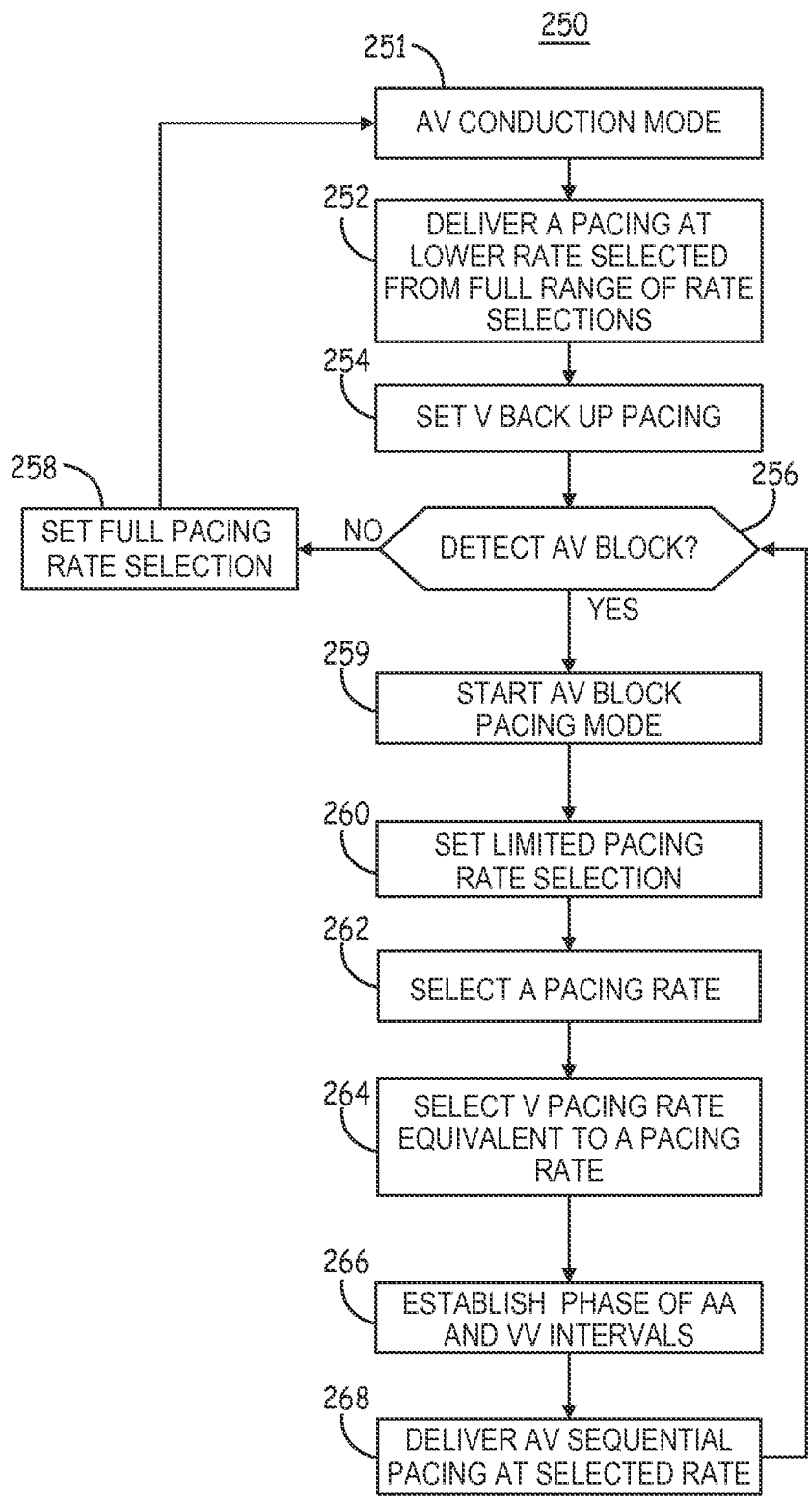
FIG. 4A is a flow chart of a method for selecting between an AV conduction pacing mode and an AV block pacing mode in a dual chamber pacing system including the separate atrial and ventricular pacemakers shown in FIG. 1.

FIG. 4A is a flow chart 250 of a method for selecting between an AV conduction pacing mode and an AV block pacing mode in a dual chamber pacing system including the separate atrial and ventricular pacemakers shown in FIG. 1. Flow chart 250 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the pacemaker 100 and by the particular detection and therapy delivery methodologies employed by the pacemaker 100. Providing software, hardware, and/or firmware to accomplish the described functionality in the context of any modern pacemaker system, given the disclosure herein, is within the abilities of one of skill in the art. Methods described in conjunction with flow charts presented herein may be implemented in a computer-readable medium that includes instructions for causing a programmable processor to carry out the methods described. The instructions may be implemented as one or more software modules, which may be executed by themselves or in combination with other software.

At block 251, the RA pacemaker 12 and the RV pacemaker 14 are operating in an AV conduction pacing mode when the intrinsic conduction pathway through the AV node is intact. During the AV conduction mode, the control module 206 of RA pacemaker 12 delivers atrial pacing pulses at block 252 as needed at a lower pacing rate, which may be a programmed base pacing rate or a temporary lower pacing rate set based on a SIR. The atrial pacing rate may be programmed to a minimum lower pacing rate (sometimes referred to a "base pacing rate") that provides bradycardia pacing, e.g., at a rate between 40 and 60 ppm. If the intrinsic atrial rate falls below the programmed lower rate, based on the absence of a P-wave during an AA pace interval, an atrial pacing pulse is delivered. If rate responsive pacing is enabled, the lower pacing rate may be adjusted to a temporary lower rate greater than the minimum lower pacing rate to support a non-resting patient activity level. The RA pacemaker 12 may be pacing in an AAIR mode at block 252, for example. The control module 206 of RA pacemaker 12 may utilize a full range of available pacing rate settings between a minimum lower pacing rate and a maximum pacing rate using the highest available resolution (smallest available step size) between pacing rates. The available programmable settings may vary between examples, but an example full pacing rate selection may include pacing rates from 50 ppm to 120 ppm available in 5 ppm increments during the AV conduction pacing mode.

In the AV conduction pacing mode, the RV pacemaker 14 may be configured to operate in a minimum ventricular pacing mode at block 254 in which the VV pacing interval is set to a relatively long backup pacing interval to allow the ventricular rate to follow the intrinsic or paced atrial rate via normal conduction through the AV node. If RA pacemaker 12 is programmed to the minimum lower pacing rate without rate response, the ventricular rate will follow the intrinsic atrial rate when the intrinsic rate rises above the minimum lower pacing rate due to the naturally conducted depolarizations via the AV node. If the intrinsic atrial rate drops below the programmed minimum lower pacing rate, the atrial pacing evoked responses occurring at the minimum lower pacing rate will be conducted to the ventricles. If rate responsive pacing is enabled, the ventricular R-waves will occur after an intrinsic AV conduction time and will follow the atrial rate, paced at a SIR, or the intrinsic atrial rate if it is higher than the adjusted temporary lower rate.

If an R-wave is not sensed during the backup VV pace interval, a backup ventricular pacing pulse is delivered. A backup VV pace interval may be set to 1500 ms for example. In some cases, the backup ventricular pacing interval may be automatically adjusted based on a sensed ventricular rate, e.g., 500 ms greater than a sensed RR interval between two consecutively sensed R-waves.

One or both of RA pacemaker 12 and the RV pacemaker 14 is configured to monitor for AV conduction block at block 256 during the AV conduction pacing mode. For example, the control module 206 of RV pacemaker 14 may detect AV block at block 256 based on the delivery of one or more backup ventricular pacing pulses. Absence of the intrinsic ventricular event (sensed R-wave) on one or more cycles (resulting in a backup pacing pulse at the relatively long backup VV pace interval) indicates AV conduction block. In other examples, the control module 206 of RV pacemaker 14 may detect AV block based on a FFAP event signal produced by FF event detector 224 without an accompanying R-wave sensed event signal produced by NF event detector 222 within an expected AV conduction time interval.

If RV pacemaker 14 detects AV block at block 256, the control module 206 of RV pacemaker 14 may be configured to signal RA pacemaker 12 that AV block is detected. RA pacemaker 12 detects AV block by detecting the signal from RV pacemaker 14. In one example, the signal from the RV pacemaker 14 may be produced as one or more ventricular pacing pulses delivered at predefined control parameters. The predefined ventricular pacing pulses are sensed by the FF event detector 224 of RA pacemaker 12. For example, a ventricular pacing pulse having a predetermined pulse width and/or pulse amplitude or two or more ventricular pacing pulses delivered at a predetermined pulse interval, which may be the backup pacing pulse interval, may be delivered by RV pacemaker 14 as a signal to RA pacemaker 12 that AV block is detected.

In other examples, the control module 206 of RA pacemaker 12 is configured to detect AV block by monitoring FFV events detected by FF event detector 224 of RA pacemaker 12. Methods for detecting AV block by RA pacemaker 12 are described below in conjunction with FIG. 10. For example, RA pacemaker 12 may detect AV block based on determining an AV conduction time, also referred to herein as an AV interval, between an atrial pacing pulse or P-wave sensed event signal produced by NF event detector 222 and a FFV sensed event signal produced by FF event detector 224. As used herein, "AV interval" refers to a time interval that is determined by control module 206 of RA pacemaker 12 or RV pacemaker 14 between a ventricular event (e.g., a near-field R-wave sensed by RV pacemaker 14 or a FFV event sensed by RA pacemaker 12) and a preceding atrial event, paced or sensed.

In contrast to the AV interval which is determined or measured by pacemaker 12 or pacemaker 14, the term "AV delay" as used herein refers to a time interval that is programmable or automatically set by the pacemaker system 10 as the targeted or desired time interval between an atrial pacing pulse and a ventricular pacing pulse. The AV delay between the atrial pacing pulse and the subsequent ventricular pacing pulse is controlled by the control module of at least one of RA pacemaker 12 or RV pacemaker 14 through adjusting the phase of the AA pacing interval relative to the VV pacing interval, as further described below. The relative phase of the AA pacing interval to the VV pacing interval may be adjusted until a measured AV interval during dual chamber pacing is within an acceptable range of the desired AV delay.

At block 256, the RA pacemaker 12 may determine the AV interval as the interval from an atrial pacing pulse or sensed P-wave to a FFV sensed event signal produced by FF event detector 224 of RA pacemaker 12 in response to sensing a FFV event, which may be an R-wave or a FF ventricular pacing pulse. A very long AV interval, a very short AV interval or a varying AV interval outside a physiological AV conduction time range may be evidence of AV block. Backup ventricular pacing pulses may be delivered due to the absence of a sensed R-wave by RV pacemaker 14 causing unexpected AV intervals.

In still other examples, RA pacemaker 12 may be configured to detect AV block at block 256 based on monitoring heart sound signals produced by sensors 212, e.g., by detecting the absence of an S1 signal following an atrial pacing pulse or sensed P-wave. The heart sound signal may be used by RA pacemaker 12 to determine an AV conduction time (which may be a time interval from the atrial pacing pulse or intrinsic P-wave to the mechanical heart sound response in the ventricle). The AV conduction time can be compared to an acceptable range or threshold and if excessively long, a degree of AV conduction block is detected. Additional methods for detecting AV block by RA pacemaker 12 are described in conjunction with FIG. 10.

In response to detecting AV block at block 256, the control module 206 of RA pacemaker 12 and the control module 206 of RV pacemaker 14 switch to an AV block pacing mode at block 259. The AV block pacing mode includes setting the available pacing rates to a limited number of pacing rates at block 260. The limited number of pacing rates available during the AV block pacing mode is less than the number of pacing rates available during the AV conduction pacing mode and therefore include a lower resolution, i.e., larger step size between pacing rates. The limited number of pacing rates may include 2, 3, 4 or another number of pacing rate selections less than the number of selections included in the full set of pacing rates used when AV conduction is intact. In one illustrative example, the selection of AV block pacing rates is set by RA pacemaker 12 at block 260 to include 60, 70, 80 and 90 ppm. Similarly, the RV pacemaker 14 is configured to set the same limited selection of available pacing rates at block 260.

The limited number of pacing rate selections set at block 260 may include a different number of available rate steps when the rate is being increased based on an increasing SIR or increasing sensed intrinsic atrial rate than the number of available rate steps available when the rate is being decreased in response to a decreasing SIR or decreasing sensed intrinsic atrial rate. At the onset of exercise, heart rate increases relatively rapidly. At the offset of exercise, during recovery, heart rate decreases relatively more slowly, i.e., over a longer period of time, than the heart rate increase at the onset of exercise. As such, fewer rate selections may be available when increasing the selected pacing rate than when decreasing the pacing rate such that a more rapid rise in pacing rate occurs with increasing SIR, and a relatively slower drop in pacing rate occurs with decreasing SIR. To illustrate, the rising pacing rate selections may include 30 ppm steps (e.g., 60 ppm, 90 ppm and 120 ppm rates) and falling pacing rate selections may include 10 ppm steps (e.g., 120 ppm through 60 ppm in 10 ppm steps). In another example, the rising pacing rate selections may include 25 ppm steps (e.g., 60 ppm, 85 ppm, and 110 ppm) and the falling pacing rate selections may include 10 ppm steps (e.g., 60 ppm, 70 ppm, 80 ppm, 90 ppm, etc.) such that both the step change and the actual rates that are selectable are different during rising pacing rate than during falling pacing rate.

At block 262, the RA pacemaker 12 selects an atrial pacing rate from the limited pacing rate selection. RA pacemaker 12 may select the atrial pacing rate from the limited selection that is equal to or the next rate higher than the SIR determined by control module 206 of RA pacemaker 12 or the next rate higher than the sensed intrinsic atrial rate, whichever is higher. At block 264, a ventricular pacing rate is established. As described in greater detail below, the ventricular pacing rate may be established as a rate that is equivalent to the atrial pacing rate based on sensing FFAP events. In other examples, the ventricular pacing rate is set based on a SIR determined by the control module 206 of RV pacemaker 14, which may be equivalent to the rate selected by RA pacemaker 12.

At block 266, the phase of the AA pace intervals (set according to the selected atrial pacing rate) relative to the VV pace intervals (set according to the established ventricular pacing rate), is adjusted by the control module 206 of RA pacemaker 12 or the control module 206 of RV pacemaker 14 to establish a desired AV delay between atrial and ventricular pacing pulses. For example, an AA or a VV pace interval may be temporarily adjusted by 10 ms, 20 ms or other increment or decrement on one or more pacing cycles until a desired AV delay is reached based on a measured AV interval. Once the desired AV delay is reached the respective AA or VV pace interval that was temporarily adjusted is reset to the selected pacing rate. Adjustment of a pacing interval phase to achieve a desired AV delay is described below.

If AV conduction returns during the AV block pacing mode, as determined at block 256, the RA pacemaker and the RV pacemaker return to the AV conduction pacing mode as described above, which includes restoring the full selection of available pacing rates at block 258.

Figure 4B:
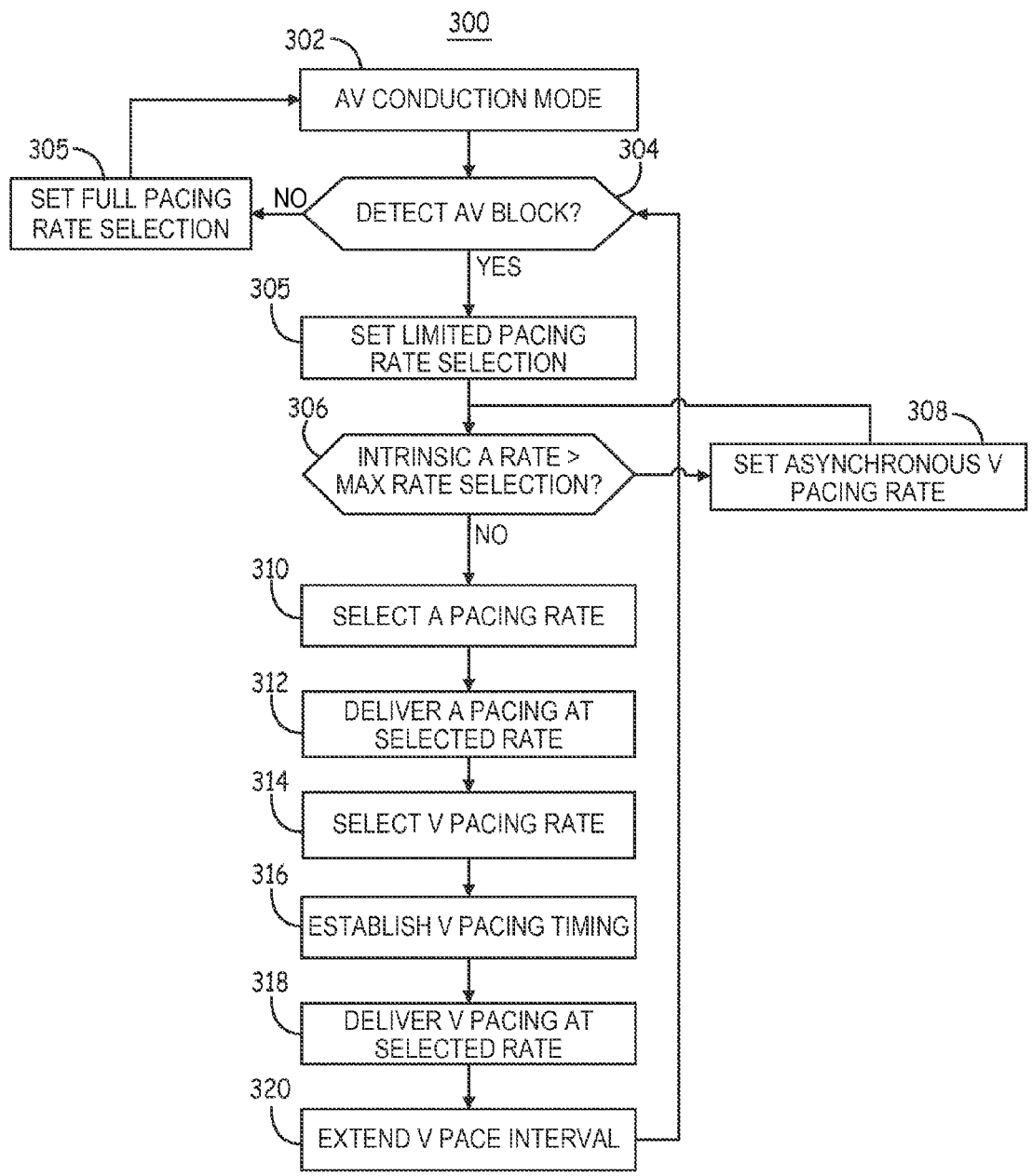
FIG. 4B is a flow chart of a method for controlling the dual chamber pacing system of FIG. 1 for delivering coordinated, AV sequential pacing.

FIG. 4B is a flow chart 300 of a method for controlling dual chamber pacing delivered by RA pacemaker 12 and RV pacemaker 14 during AV block according to one example. At block 302, the RA pacemaker 12 and the RV pacemaker 14 are operating in the AV conduction pacing mode as described above. Briefly, the RA pacemaker 12 delivers atrial pacing pulses as needed utilizing a full range of available pacing rate selections. RV pacemaker 14 provides only backup ventricular pacing as needed.

If AV block is detected at block 304 (as described in conjunction with FIG. 4A or FIG. 10), the RA pacemaker 12 and the RV pacemaker 14 each set a limited pacing rate selection at block 305 including fewer available pacing rates than the full pacing rate selection used during the AV conduction pacing mode. RA pacemaker 12 determines at block 306 whether the intrinsic atrial rate is greater than the highest available pacing rate of the limited rate selection. If the intrinsic atrial rate is higher than any of the available pacing rates or greater than an atrial tachyarrhythmia detection rate, RA pacemaker 12 may select an arbitrary rate of the available pacing rates, e.g., the highest available pacing rate, lowest available pacing rate or any rate there between until the intrinsic atrial rate is less than the highest rate of the limited pacing rate selection.

In this situation, the RV pacemaker 14 may select the ventricular pacing rate at block 308 based on the SIR determined by control module 206 of RV pacemaker 14 and pace the ventricle asynchronously until the intrinsic atrial rate drops below the highest available pacing rate selection.

As will be described below, the RA pacemaker 12 may signal the RV pacemaker 14 of a selected atrial pacing rate by delivering one or more high output atrial pacing pulses sensed as FFAP events by RV pacemaker 14. If RV pacemaker 14 detects AV block but does not sense FFAP events (due to inhibited atrial pacing during the high intrinsic atrial rate), the RV may select the ventricular pacing rate from the limited pacing rate selection based on a programmed base rate or the SIR determined by control module 206 of RV pacemaker 14 and pace the ventricle asynchronously with the atria during the high atrial rate.

If the intrinsic atrial rate is less than the highest available pacing rate of the limited pacing rate selection, as determined at block 306, the RA pacemaker 12 selects the atrial pacing rate at block 310 from the limited rate selection. The atrial pacing rate is set to the next pacing rate higher than the sensed intrinsic atrial rate or the SIR determined by RA pacemaker 12, whichever is greater. RA pacemaker 12 begins delivering the atrial pacing pulses at the selected rate at block 312. As described in greater detail in conjunction with FIG. 5, the RA pacemaker 12 controls its pulse generator 202 to deliver the atrial pacing pulses initially at a high pulse amplitude and/or width to enable RV pacemaker 14 to sense the FFAP events at block 314. The RV pacemaker 14 selects a ventricular pacing rate from the limited pacing rate selection at block 305 that is equivalent to the selected atrial rate based on the sensed FFAP event intervals.

In other examples, the control module 206 of each pacemaker 12 and 14 may determine a SIR from its own rate response sensor signal. Each pacemaker 12 and 14 may determine a SIR and set the respective pacing rate to the next highest pacing rate available from the limited pacing rate selections. For example, if the SIR is 84 ppm, the control module 206 of RA pacemaker 12 may set the atrial pacing rate to 90 ppm. It may be assumed that the control module 206 of RV pacemaker 14 determines the same or similar SIR and will therefore select a ventricular pacing rate from the limited pacing rate selection that is greater than the SIR determined by RV pacemaker 14 and equal to the pacing rate selected by RA pacemaker 12.

Assuming each of the RA pacemaker 12 and the RV pacemaker 14 select the same pacing rate, the control module 206 of RV pacemaker 14 may wait for the first RA pacing pulse to be delivered at block 312 to establish the correct phase of the ventricular pace intervals relative to the atrial pace intervals at block 316. The FF event detector 224 may sense the RA pacing pulse and produce a FFAP sensed event signal that is passed to control module 206 of RV pacemaker 14. Control module 206 may control pulse generator 202 to deliver a ventricular pacing pulse at a programmed AV delay after the atrial pacing pulse at block 316. The RV pacemaker 14 may then continue delivering ventricular pacing pulses at the selected ventricular pacing rate at block 318.

In this way, the RA pacemaker 12 and the RV pacemaker 14 are both delivering pacing pulses at the same rate, selected from the same limited selection of pacing rates to be greater than the respectively determined SIRs in each device. The phase of the pacing pulses delivered in each chamber is established by timing at least the first ventricular pacing pulse at a desired AV delay after an atrial pacing pulse as established at block 316. In other cases, the desired AV delay is established by adjusting the phase of the VV pace interval relative to the AA pace interval or vice versa as described in greater detail below.

In some instances, the sensed intrinsic atrial rate is greater than the SIR determined by the RA pacemaker 12. The RV pacemaker 14 may therefore wait to select the ventricular pacing rate at block 314 after atrial pacing is started at block 312 at the selected atrial pacing rate. The RV pacemaker 14 senses the FFAP events to determine a FFAP interval used for selecting the correct rate to pace the ventricles, which is equivalent to the selected atrial pacing rate. In other examples, the RV pacemaker 14 may initially set the ventricular pacing rate based on a SIR determined by the RV pacemaker 14 then adjust the ventricular pacing rate as needed based on a rate of FFAP sensed events at block 314 after atrial pacing and ventricular pacing have started at the separately selected rates.

As indicated above, after selecting a pacing rate at block 310, the control module 206 of RA pacemaker 12 may control pulse generator 202 to deliver at least one atrial pacing pulse at block 312 at a predetermined pacing pulse amplitude (and/or width) that promotes detection by FF event detector 224 of RV pacemaker 14 for use in establishing the ventricular pacing pulse timing relative to the atrial pacing pulse at block 312. For example, the RA pacemaker 12 may deliver a relatively high output pacing pulse (amplitude and/or width), e.g., a 5 Volt pacing pulse, for one, two, three of more consecutive pacing cycles to be detected by FF event detector 224 of RV pacemaker 14. The control module 206 of RV pacemaker 14 may then adjust the VV pace interval on one or more pacing cycles to establish a desired AV delay then continue pacing at the selected ventricular rate, which is equivalent to the selected atrial pacing rate.

In some cases, the RA pacemaker 12 may periodically repeat delivery of one or more high output pacing pulses to allow RV pacemaker 14 to adjust the timing of the ventricular pacing pulses on one or more pacing cycles as needed to restore and maintain a desired AV delay then return to the selected ventricular pacing rate. For example, the control module 206 of RV pacemaker 14 may temporarily adjust the VV pace interval by 10 ms, 20 ms, or other step change for one or more cardiac cycles in order to shift the phase of the VV pace interval relative to the AA pace interval over one or more cycles until a ventricular pacing pulse is delivered at the desired AV delay after the high output atrial pacing pulse. The next ventricular pacing pulse is scheduled at the selected VV pace interval to restore the selected ventricular pacing rate equivalent to the atrial pacing rate.

In some examples, the RA pacemaker 12 may be configured to deliver the RA pacing pulses at a high pacing output and monitor the AV interval, determined as the AP-FFV interval, until a measured interval between the atrial pacing pulse and a sensed FFV event meets an acceptable AV delay. The RV pacemaker 14 may deliver ventricular pacing pulses at an adjusted VV pace interval until a measured AV interval between a FFAP event and the delivered ventricular pacing pulse meets the acceptable AV delay. In this way, RV pacemaker 14 and RA pacemaker 12 may operate cooperatively to enable RV pacemaker 14 to adjust the VV pace interval over one or more pacing cycles to establish the desired phase between atrial and ventricular pace intervals at block 316 that results in the desired AV delay. In other examples, the RA pacemaker 12 adjusts the phase of the AA pace interval relative to the FFV sensed event interval until a desired AV delay is reached.

In some cases, the RV pacemaker 14 may select a pacing rate that is greater than the pacing rate selected by RA pacemaker 12 due to differences in the SIR determined by each pacemaker. For example, RA pacemaker 12 may determine a SIR of 78 and select an atrial pacing rate of 80 ppm.

RV pacemaker 14 may determine a SIR of 82 and select a ventricular pacing rate of 90 ppm. In these cases, different asynchronous pacing rates may be accepted since the higher ventricular pacing rate may be considered greater priority for patient benefit than A-V sequential pacing. In other examples, the RA pacemaker 12 may monitor FFV sensed events and recognize that the RV pacemaker 14 has selected a higher rate and adjust the selected atrial pacing rate to match the selected ventricular pacing rate.

The RA pacemaker 12 may select the higher one of the selected atrial pacing rate and the selected ventricular pacing rate, which can be identified by RA pacemaker 12 based on a rate of sensed FFV events. However, if the sensed intrinsic atrial rate is greater still, the RA pacemaker 12 may select a pacing rate higher than the sensed atrial rate and signal the rate selection to the RV pacemaker 14, e.g., by delivering high output pacing pulses at the selected rate. The RV pacemaker 14 may then adjust its selected pacing rate accordingly. As such, the atrial pacing rate selection made at block 310, the ventricular pacing rate selection made at block 314 and the process of establishing timing of the ventricular pacing pulses relative to atrial pacing pulses at a desired AV delay may be performed over multiple cardiac cycles as the RA pacemaker 12 and/or RV pacemaker 14 monitor FF signals for detecting the FF event rate and/or deliver high output pulses for signaling an appropriate rate selection to the other pacemaker and/or to facilitate establishing the desired AV delay.

During the AV block pacing mode, the RV pacemaker 14 may periodically extend one or more pacing escape intervals at block 320 to determine if AV conduction has returned. If AV conduction has not returned, the RA pacemaker 12 and RV pacemaker 14 remain in the AV block pacing mode using the limited pacing rate selection. RV pacemaker 14 may detect a return of AV conduction based on sensing an R-wave by NF event detector 222. In response to sensing an R-wave on one or more pacing cycles, the RV pacemaker 14 may return to a backup pacing mode at block 302 to provide minimum ventricular pacing and promote natural AV conduction.

In some examples, RV pacemaker 14 may signal RA pacemaker 12 that AV block is no longer detected at block 304. RV pacemaker 14 may signal AV conduction has returned by delivering one or more ventricular pacing pulses at a predetermined pulse amplitude and/or width. In other examples, the RA pacemaker telemetry module 208 may be configured to listen for a communication signal from the RV pacemaker telemetry module 208 at scheduled intervals that correspond to scheduled AV conduction checks performed by RV pacemaker 14. RV pacemaker 14 may transmit a wireless communication signal to RA pacemaker 12 that indicates AV conduction has returned.

In other examples, the RA pacemaker 12 may detect a return of AV conduction at block 304 by determining the interval between an atrial pacing pulse and a FF event sensed by FF event detector 224 of RA pacemaker 12. In some examples, the RA pacemaker 12 and the RV pacemaker 14 may be configured to redetect AV block on a synchronized, scheduled basis. For example, the RV pacemaker 14 may be configured to extend a VV pacing escape interval after every nth pacing pulse. The RA pacemaker 12 may be configured to determine an AV interval between atrial pacing pulse and subsequent FF sensed event. If the determined AV interval is greater than a physiological AV conduction time, AV block is still detected and the RA pacemaker 12 remains in the AV block pacing mode.

In other examples, the RA pacemaker 12 may alter the pacing rate on a scheduled basis to determine if an interval between the RA pacing pulse and a FF sensed event signal remains approximately the same. If not, the RV pacemaker 14 is pacing independently of the atrial pacing rate. If a FF sensed event occurs at approximately the same interval after atrial pacing pulses delivered at varying intervals, AV conduction has returned.

If AV block is no longer detected at block 304, the RA pacemaker 12 returns to a full pacing rate selection at block 304 for use during atrial pacing at block 302. The RA pacemaker 12 returns to a normal operating mode for AV conduction using the full range of available pacing rates selectable at finer pacing rate increments for setting the atrial pacing rate and may periodically extend the atrial pace interval to allow intrinsic atrial activity to drive the heart rate whenever a normal sinus rate is being produced by the intrinsic conduction system. If AV block is detected again, the RA pacemaker 12 and RV pacemaker 14 return to the AV block pacing mode by again setting a limited pacing rate selection at block 305.

During the AV block pacing mode, if the patient's activity level changes, it is assumed that each RA pacemaker 12 and RV pacemaker 14 will determine a new SIR and select the next higher pacing rate from the limited pacing rate selection. In this way, both devices will continue pacing at matching rates as long as AV block is being detected, even though that rate may change as the SIR changes, as described below in conjunction with FIG. 6. If RA pacemaker 12 changes from one of the limited pacing rate settings to another one of the limited pacing rate settings due to a change in SIR or a change in the sensed intrinsic rate, the first one or more pacing pulses may be set to a high pacing output to promote reliable sensing of the FF atrial pacing pulses by the RV pacemaker 14 for establishing V pace timing relative to the atrial pacing pulses at the adjusted rate.

Figure 5:
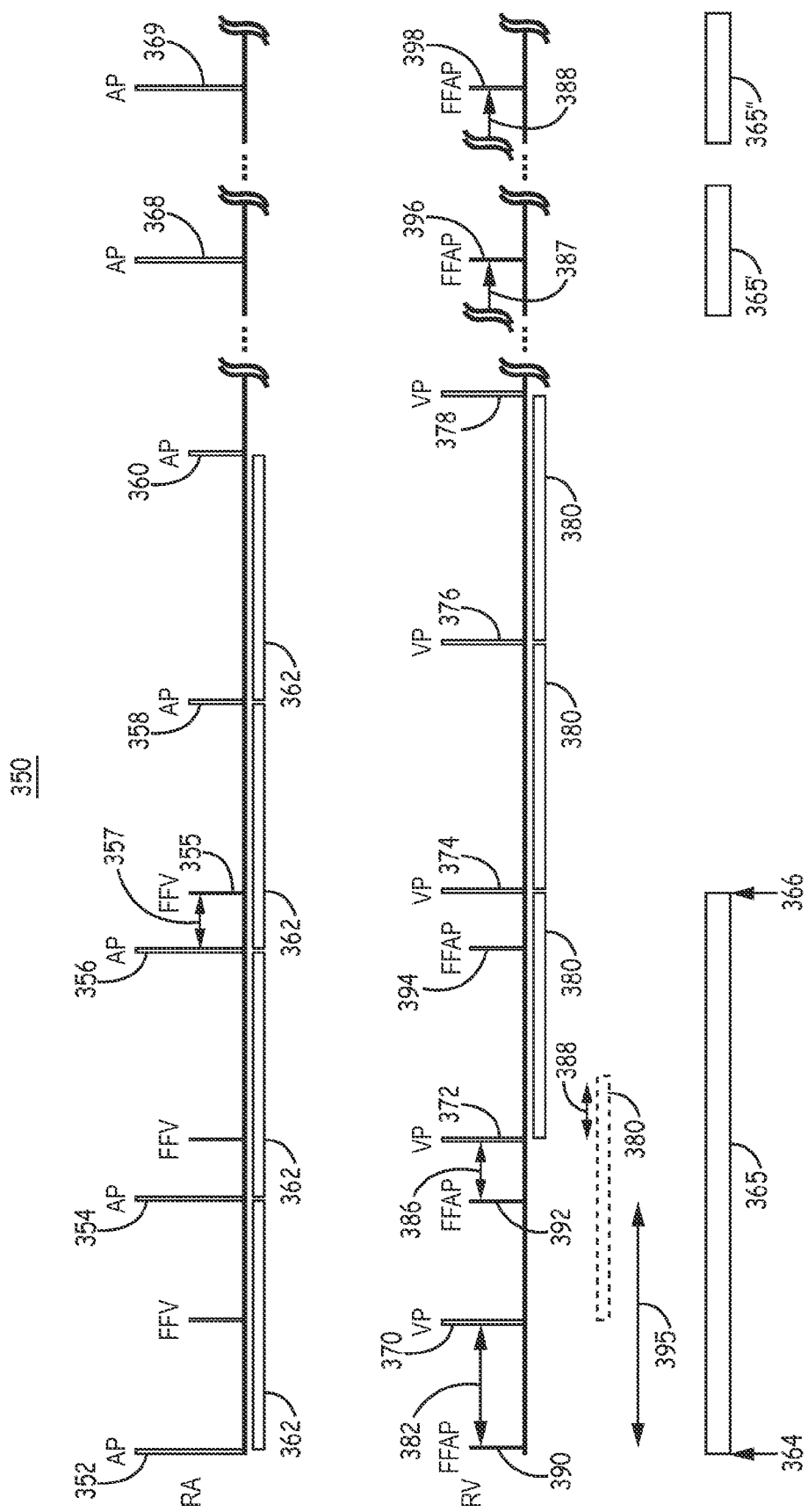
FIG. 5 is a timing diagram of atrial and ventricular pacing pulses delivered by the system of FIG. 1 after a pacing rate adjustment.

FIG. 5 is a timing diagram 350 of atrial and ventricular pacing pulses delivered by RA pacemaker 12 and RV pacemaker 14 after a rate adjustment during the AV block pacing mode. RA pacemaker 12 selects a pacing rate from the limited pacing rate selection in response to detecting AV block, either directly by analyzing FFV sensed events or based on a communication signal from RV pacemaker 14. The selected pacing rate is selected to be greater than the intrinsic atrial rate so that the RA pacemaker 12 is driving the atrial rate. The AA pace interval 362 is set according to the selected pacing rate. Atrial pacing pulses 352, 354, 356, 358 and 360 are all delivered at the AA pace interval 362, i.e., at the selected atrial pacing rate.

The first three atrial pacing pulses 352, 354 and 356 are delivered at a high pacing pulse output, e.g., 5 Volts. The sensing module 204 of RV pacemaker 14 senses the atrial pacing pulses 352, 354 and 356 as FFAP sensed events 390, 392 and 394. The control module 206 of RV pacemaker 14 may be configured to detect AV block based on an absence of sensed R-waves or backup ventricular pacing pulse delivery and to monitor for FFAP sensed events following the AV block detection. The FFAP sensed events may be used for establishing the selected ventricular pacing rate and/or for adjusting the phase of the VV pace interval relative to the AA pace interval to establish a desired AV delay. For example, if RV pacemaker 14 detects AV block at time 364, FF event detector 224 may be enabled for sensing FF atrial pacing pulses. The power provided to an amplifier of sensing module 204 may be increased at block 364 to enable FFAP event sensing during time period 365.

The RV pacemaker 14 may select a ventricular rate based on a currently-determined SIR as described above. Alternatively, RV pacemaker 14 may provide backup ventricular pacing pulses while monitoring for FFAP sensed events 390, 392 and 394 during time interval 365. FFAP event sensing is enabled for determining a time interval 395 between FFAP sensed events 390 and 392. Time interval 395 is identified by the control module 206 of RV pacemaker 14 as the AA pacing interval and used by the control module 206 of RV pacemaker 14 to set the VV pace interval 380. VV pace interval 380 matches AA pace interval 362 and corresponds to a selected ventricular pacing rate of the limited pacing rate selection that matches or is equivalent to the selected atrial pacing rate.

In the example shown, the first ventricular pacing pulse 370 may be a backup ventricular pacing pulse. The RV control module 206 may control pulse generator 202 to control the first pacing pulse 372 that starts the selected VV pace interval 380 to be delivered at a desired AV delay 386 after FFAP sensed event 392 thereby setting the phase of subsequent VV pace intervals 380 relative to AA pace intervals 362. In this way, AV synchronous pacing is delivered with each ventricular pacing pulse 374, 376 and 378 following respective preceding atrial pacing pulses 356, 358, and 360 at the desired AV delay 386. The phase of the VV pace interval 380 is set based on FFAP sensed events 390, 392, and 394 sensed during time interval 365 when FF event detector 224 of RV pacemaker 14 is enabled.

Once the ventricular rate is selected and the phase of the VV pace interval 380 is set relative to the AA pace interval 362 (based on FFAP sensed events 390, 392 and 394), the control module 206 of RV pacemaker 14 may disable FF event detector 224 at time 366, terminating the time interval 365. Time interval 365 may be a fixed time interval during which at least three (or other desired number) of the FF atrial pacing pulses can be sensed. In other examples, time interval 365 is a variable interval that is terminated at time 366 once RV pacemaker 14 has sensed enough FFAP events to allow the ventricular pacing rate to be selected and the VV pace interval phase relative to the AA pace interval to be set to result in the desired AV delay 386. Power source 214 of RV pacemaker 14 is conserved by sensing FF events only when needed for establishing the ventricular rate and/or AV delay 386.

Thereafter, RV pacemaker 14 does not need to sense FF atrial pacing pulses on each cardiac cycle. As such, atrial pacing pulses 358 and 360 may be delivered at a lower output, e.g., lower voltage, than the initial three pulses 352, 354 and 356. The amplitude of subsequent pacing pulses 358 and 360 may be set based on an atrial pacing capture threshold determined by RA pacemaker 12 to conserve power source 214 of RA pacemaker 12.

In other examples, upon detecting AV block, the RV pacemaker 14 selects the ventricular pacing rate based on the SIR determined by RV pacemaker 14 without relying on FFAP sensed events 390, 392 and 394. The FFAP sensed events 390, 392, and 394 may be used, however, for establishing the phase of the ventricular pace interval 380. Ventricular pacing pulse 370 may be delivered as a backup pacing pulse or may be the first pacing pulse delivered at the selected ventricular pacing rate. In either case, control module 206 of RV pacemaker 14 may determine the time interval 382 between FFAP sensed event 390 and the ventricular pacing pulse 370. The difference 388 between this time interval 382 and a desired AV delay 386 is subtracted from the VV pace escape interval 380 (or added if time interval 382 is shorter than the desired AV delay) so that the next ventricular pacing pulse 372 is delivered at the desired AV delay 386 after FFAP sensed event 392. The RV pacemaker 14 continues to operate in a VVI pacing mode thereafter delivering ventricular pacing pulses 374, 376 and 378 at VV pace intervals 380 which have a desired phase relative to AA pace intervals 362 without requiring or setting an AV delay timer or sensing FFAP events on a continuous beat-by-beat basis.

In some examples, the control module 206 of RA pacemaker 12 is configured to deliver high output pacing pulses 352, 354 and 356 according to a predefined schedule, e.g. after every one minute or other predetermined time interval or number of pacing pulses. The control module 206 of RV pacemaker 14 is configured to start time interval 365 to enable FF event sensing according to the same predefined schedule, e.g., after every one minute or a predetermined number of ventricular pacing pulses. This scheduled time for high output atrial pacing pulses 352, 354, and 356 concurrently with time interval 365 (during with FF event detector 224 of RV pacemaker 14 is enabled) permits RA pacemaker 12 and RV pacemaker 14 to operate cooperatively in establishing synchronized AV sequential pacing.

RA pacemaker 12 may be configured to change the selected pacing rate only at this scheduled time, e.g., after every one minute or a predetermined number of atrial pacing pulses, so that RV pacemaker 14 will be enabled to monitor for FFAP events for detecting a pacing rate change based on the FFAP sensed event interval 395. At times, RA pacemaker may be increasing the selected atrial pacing rate, e.g. due to a change in the SIR or an increase in sensed intrinsic P-waves. At other times, RA pacemaker 12 may be decreasing the selected atrial pacing rate to test whether the intrinsic atrial rate has decreased and if a lower atrial pacing rate will still adequately overdrive pace the atrium.

If RA pacemaker 12 does not need to change the atrial pacing rate, the high output atrial pacing pulses 352, 354 and 356 may still be delivered according to the predetermined schedule to enable RV pacemaker 14 to make any adjustments to the phase of the VV pace interval 380 to re-establish the desired AV delay 386. RA pacemaker 12 may deliver more than the three high output pacing pulses 352, 354 and 356 shown in FIG. 5 at scheduled intervals. In some cases, the number of high output pacing pulses is not fixed. RA pacemaker 12 may enable FF event detector 224 to sense FF ventricular events during time interval 365 so that RA pacemaker 12 can determine the time interval 357 from an atrial pacing pulse 356 to a sensed FF ventricular event 355. Once the time interval 357 has reached a desired AV delay, following at least one or more atrial pacing pulses, e.g., pulses 354 and 356, RA pacemaker 12 may switch to normal output pacing pulses 358 and 360 delivered at the selected pacing rate.

In some instances, a clock included in control module 206 of RA pacemaker 12 and a clock included in control module 206 of RV pacemaker 14 may not be operating at exactly the same frequency. Even though both the RA pacemaker 12 and the RV pacemaker 14 have selected the same pacing rate, the phase of the VV pace interval 380 relative to the AA pace interval 362 may drift over multiple pacing cycles. For example, just a 1% difference in the clock frequencies may cause a shift in the relative phase of the pace intervals 362 and 380 of 10 ms/sec, which left uncorrected could lead to an undesirable AV delay. By regularly scheduling high output atrial pacing pulses and FF event sensing time interval 365, the RV pacemaker 14 may regularly re-establish the desired AV delay by adjusting the phase of the VV pace interval 380 to avoid undesirable AV delays. The phase of the VV pace interval 380 may be adjusted by increasing or decreasing the VV pace interval by a single step on one cardiac cycle to reset the desired AV delay then restoring the VV pace interval on the next cardiac cycle. Alternatively, the VV pace interval 380 may be adjusted by a multiple step changes over multiple cardiac cycles until the desired AV delay is reached and the VV pace interval is then restored to the selected ventricular pacing rate.

In another example, the RV pacemaker 14 may determine the total time from a first high output pacing pulse 352 (sensed as FFAP event 390) to a last high output pacing pulse 356 (sensed as FFAP event 394 and compare this time interval to an expected time interval. For example, if RV pacemaker 14 has selected a pacing rate of 60 ppm the first FFAP sensed event 390 and the last FFAP sensed event 394 are expected to be 2000 ms apart. If the actual time interval is different than 2000 ms, the RV pacemaker 14 may make an adjustment to VV pace interval 380 to correct for a difference in clock cycle frequencies.

In various examples, the number of pacing cycles between the first and last FFAP sensed events used to adjust the VV pace interval 380 may differ. For example, whenever the selected pacing rate is changed by RA pacemaker 12, the control module of RA pacemaker 12 may schedule at least the first atrial pacing pulse 352 and the tenth atrial pacing pulse 368 to be high output pacing pulses. Some or all intervening atrial pacing pulses (e.g., the fourth atrial pacing pulse 358 shown in FIG. 5 through the ninth pacing pulse) may be delivered at a normal pacing pulse output. RV pacemaker 14 may re-enable a FF event sensing window 365 to encompass a time that the tenth FFAP event 396 is expected. A time interval 387 between the first FFAP sensed event 390 to the tenth FFAP sensed event 396 is determined by RV pacemaker control module 206 and compared to an expected time interval, e.g., 9 seconds if the pacing rate is 60 ppm. If the actual time interval 387 is different than the expected time interval, the VV pace interval 380 may be adjusted by one-ninth of the difference from the expected time interval to correct for a difference in the pacemaker clock cycle frequencies.

This procedure may be repeated, using the same or a different number of pacing cycles to further refine the ventricular pace interval 380 as needed to account for clock cycle frequency differences. For example, after refining the VV pace interval 380 based on the first and tenth FFAP sensed events 390 and 396, the RA pacemaker 12 may increase the pacing output on the thirtieth atrial pacing pulse 369 after the tenth atrial pacing pulse 368. Intervening atrial pacing pulses may be delivered at the normal pacing output and may or may not be sensed by RV pacemaker 14. It may be desirable to avoid sensing normal atrial pacing pulses and only sense high output atrial pacing pulses by RV pacemaker 14. As such, sensing module 204 may be controlled by control module 206 to set the sensing threshold of FF event detector 224 to a threshold that allows high output atrial pacing pulses to be detected as FFAP events and normal output atrial pacing pulses to go undetected.

The RV pacemaker 14 may be configured to enable a FFAP event sensing window 365" encompassing the time that the thirtieth atrial pacing pulse 369 is expected to be sensed. The control module 206 of RV pacemaker 14 determines the time interval 388 from the FFAP sensed event 396 corresponding to the tenth atrial pacing pulse 368 to the time of the FFAP sensed event 398 corresponding to the thirtieth atrial pacing pulse 369. The determined actual time interval 388 is compared to an expected time. A difference between the actual time interval 388 and the expected time interval (19 times the current VV pace interval) indicates a difference in the clock cycle frequencies. This difference is used to further refine the VV pace interval 380 to match the duration of the AA pace interval 362. The clock cycle frequency difference may be determined by dividing the difference between the actual time interval 388 and the expected time interval by the number of pacing cycles during the actual time interval. In some examples, a clock cycle frequency difference determined by RV pacemaker 14 may be stored and used to adjust the VV pace interval 380 as needed when new pacing rates are selected without repeating the procedure of determining a discrepancy in clock cycle frequencies every time a rate change is made.

In some cases, RV pacemaker 14 may withhold a ventricular pacing pulse during the FF event sensing time interval 365 to detect a return of AV conduction. For example, if time interval 365 is being started at a scheduled time, e.g., after one minute or after delivering a predefined number of ventricular pacing pulses (and not in response to an immediate AV block detection), the control module 206 may inhibit or delay at least one ventricular pacing pulse during time interval 365 while FFAP sensed event interval 395 is being determined. The FFAP sensed events 390, 392 and 394 during time interval 365 may be used to set an R-wave sensing window for looking for an intrinsic R-wave when one or more of ventricular pacing pulses 370, 372 and 374 are withheld. If NF event detector 222 of RV pacemaker 14 produces at least one R-wave sensed event signal, the control module 206 of RV pacemaker 14 may detect a return of AV conduction and switch the RV pacemaker pacing mode to a minimum ventricular pacing backup pacing mode in accordance with the AV conduction mode described previously herein.

In the timing diagram of FIG. 5, the RV pacemaker 14 is described as adjusting a phase of the VV pace interval 380 relative to the AA pace interval 362 to establish a desired AV delay. It is recognized that in other embodiments, the RA pacemaker 12 may adjust the phase of the AA interval 362 relative to the VV interval 380 based on determining the AP-FFV interval 357 and delivering one or more shortened or lengthened AA intervals as needed until the AP-FFV interval 357 is within an acceptable range of the desired AV delay. Adjustment of the AA pace interval to establish a desired AV delay is generally disclosed in U.S. patent application Ser. No. 14/227,962, filed on Mar. 27, 2014 (Demmer, et al.), incorporated herein by reference in its entirety.

Figure 6:
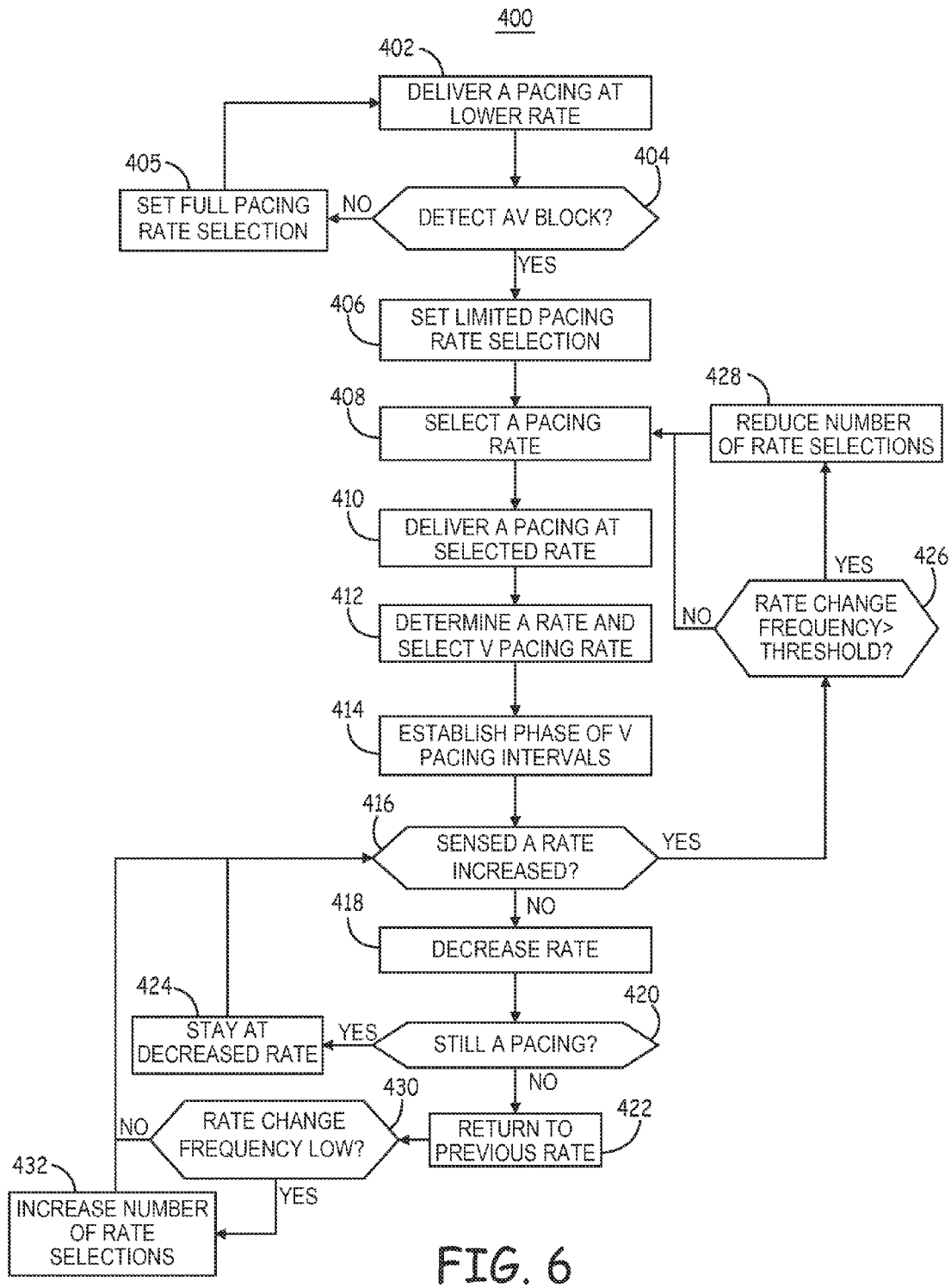
FIG. 6 is a flow chart of a method for controlling dual chamber pacing delivered by the system of FIG. 1 during AV block.

FIG. 6 is a flow chart 400 of a method for controlling dual chamber pacing delivered by RA pacemaker 12 and RV pacemaker 14 during AV block. Atrial pacing is delivered as needed by RA pacemaker 12 according to a programmed lower rate at block 402 as long as AV conduction is intact during AV conduction mode pacing. Backup ventricular pacing is provided in a minimum ventricular pacing mode that allows intrinsic conduction through the AV node to occur. If AV block is detected at block 404, as described in conjunction with FIG. 4A or FIG. 10, a limited pacing rate selection is set at block 406 by RA pacemaker 12 and RV pacemaker 14. The control module 206 of RA pacemaker 12 selects an atrial pacing rate from the limited pacing rates at block 408.

In order to promote AV synchronous pacing during AV block, both the RA pacemaker 12 and the RV pacemaker 14 are configured to select a common pacing rate. In some cases, rate responsive pacing may be disabled or the atrial intrinsic rate may be faster than a SIR determined by the RA pacemaker and/or RV pacemaker control modules. The control module 206 of RA pacemaker 12 determines the atrial intrinsic rate and sets the atrial pacing rate to the lowest pacing rate available from the limited selection of pacing rates that is greater than the intrinsic atrial rate to effectively take control of the heart rate. For example, if the intrinsic rate is 64 beats per minute (bpm) based on P-wave sensed event signals produced by NF event detector 222, the control module 206 of RA pacemaker 12 selects the atrial pacing rate to be 70 ppm or whatever lowest rate is available from the limited rate selection that is greater than 64 bpm.

The control module 206 of RA pacemaker 12 controls pulse generator 202 to deliver atrial pacing pulses at the selected pacing rate at block 410. Initially, atrial pacing pulses are delivered at a high pacing output, e.g., at a high pacing pulse amplitude such as 5 Volts. RV pacemaker 14 senses the FF atrial pacing pulses and determines a FF atrial pace interval between the sensed FFAP events. The RV pacemaker 14 sets the ventricular pacing interval to match the FFAP event interval, thereby selecting the ventricular pacing rate to match the sensed FF atrial pacing rate at block 412.

In some examples three or more atrial pacing pulses are delivered at a high pacing pulse output for atrial pacing rate detection by the RV pacemaker 14. If one atrial pacing pulse goes unsensed by RV pacemaker 14, the long FF atrial pace interval is recognized by the RV pacemaker control module 206 as a rate that is half of one of the available rate selections and therefore doubles the detected FF atrial pace interval rate to set the ventricular pacing rate. At block 414, the RV pacemaker 14 establishes the phase of the VV pace intervals relative to the AA pace intervals so that the ventricular pacing pulses follow the atrial pacing pulses at a desired AV delay.

If the intrinsic atrial rate increases during pacing at the selected rate, as determined at block 416, the control module 206 of RA pacemaker 12 will receive P-wave sensed event signals from NF event detector 222. Upon receiving P-wave sensed event signals, e.g., upon receiving at least two or another predetermined number of P-wave sensed event signals either consecutively or within a predetermined number of pacing cycles, the RA pacemaker 12 may return to block 408 to select a new, higher atrial pacing rate. In some examples, the RA pacemaker 12 may signal the RV pacemaker 14 that a rate change is about to occur using a coded electrical pulse signal pattern, a wireless telemetry signal, acoustic ping, or other coded rate change signal as described below in conjunction with FIGS. 7 and 8.

As described above, the first one, two, three or other selected number of atrial pacing pulses delivered at the newly selected rate may be delivered at a high output, e.g., 5 Volt amplitude, at block 410 to cause RV pacemaker 14 to detect the FF atrial pacing pulses at the new rate at block 412, select a new ventricular rate from the limited pacing rate selection at block 412, and re-establish the ventricular pacing phase relative to the atrial pacing pulses as needed at block 414.

In other examples, the higher intrinsic atrial rate that is asynchronous with a ventricular pacing rate may be tolerated without adjusting the atrial rate, particularly if the intrinsic atrial rate is determined to be a rate in an atrial tachyarrhythmia rate zone. If the higher intrinsic atrial rate is not in an atrial tachyarrhythmia rate zone, a maximum time limit that an atrial intrinsic rate that is greater than a selected pacing rate is tolerated may be set. After this maximum time expires, the RA pacemaker 12 may select a new atrial pacing rate that is greater than the sensed intrinsic rate by returning to block 408. In other examples, the RA pacemaker 12 may monitor the time interval between sensed atrial P-waves and FFV sensed events at block 416. If this time interval becomes greater than or less than an acceptable AV delay range (e.g., an acceptable AV delay range of 100 to 300 ms), the RA pacemaker 12 may return to block 408 to select a new atrial pacing rate from the limited rate selection that is greater than the intrinsic atrial rate to re-establish synchronized, sequential AV pacing.

The RA pacemaker control module 206 may be configured to track the frequency of increasing rate changes during the AV pacing mode at block 426. If rate changes are occurring frequently, the limited pacing rate selection may be further limited at block 428 to reduce the frequency of rate changes during AV block. For example, if a rate change is required more than twice per minute or other higher predetermined limit, as determined at block 426, the RA pacemaker 12 may reduce the number of rate selections at block 428.

In some examples, the RV pacemaker 14 does not change the limited ventricular pacing rate selections since those rates include the narrower rate selection made by the RA pacemaker 12. The RV pacemaker 14 will select a rate that matches the rate selected by the RA pacemaker 12 from its narrowed rate selections. For example, if the limited rate selection initially includes rates between 60 ppm and 90 ppm in 10 ppm increments, a narrowed rate selection may include only 60 and 90 ppm. The RA pacemaker 12 will select which of the two rates to use and the RV pacemaker will select either 60 or 90 ppm at block 412 from the available ventricular rates of 60, 70, 80 and 90.

In other examples, the RV pacemaker 14 could also track the frequency of rate changes and detect a rate change frequency that is greater than a threshold frequency at block 426 at the same time that the RA pacemaker 12 detects the high rate change frequency. Both the RA pacemaker 12 and the RV pacemaker 14 may reduce the rate selection at block 428. This adjustment by both pacemakers 12 and 14 enables one or more different rates to be included in the second, more limited rate selection than the original rate selection. For example, if the initial limited rate selection includes rates of 60 ppm through 90 ppm in 10 ppm increments, the reduced rate selection at block 428 may include 65 ppm and 85 ppm.

In other examples, instead of only determining a frequency of rate changes, the number of oscillations of rate changes between higher and lower rates is tracked at block 426 and compared to a previously defined oscillation limit. At the onset or offset of exercise, a series of increasing rate changes or a series of decreasing rate changes is expected that could result in frequent, but monotonically changing rate adjustments. Frequent oscillations in rate, i.e., a change from a high rate to a low rate to a high rate to a low rate, and so on, may be undesirable. The number of times consecutive high-low transitions or low-high transitions are made may be counted at block 426 and compared to a rate change limit, for example a limit of two oscillations (high-low-high-low) per minute. If excessive rate oscillations occur, the rate selection may be further reduced at block 428.

If the sensed atrial rate does not increase above the selected pacing rate within a predetermined period of time or number of pacing cycles, as determined at block 416, the RA pacemaker 12 and RV pacemaker 14 may be configured to decrease the respective atrial pacing rate and ventricular pacing rate to the next lower pacing rate available from the limited pacing rate selections. The RA pacemaker 12 and the RV pacemaker 14 may each be programmed to follow a common protocol for attempting a lower pacing rate. For example, each pacemaker 12 and 14 may be scheduled to attempt a lower pacing rate after a predetermined number of pacing pulses at a given rate, e.g., after approximately one minute. To illustrate, if the rate selected at blocks 408 and 412 is 80 ppm, after one minute or another predetermined time interval or number of pacing pulses, the AA pace interval and the VV pace interval may each be increased to deliver the next pacing pulse in the respective RA and RV chambers at the next lower available rate, e.g., 70 ppm. One or more pacing pulses may be delivered at the lower rate at block 418. The RA pacemaker 12 determines if intrinsic P-wave events are sensed at block 420 resulting in inhibited atrial pacing or if atrial pacing pulses continue at the decreased rate without atrial sensed events.

If atrial sensing occurs, causing atrial pacing pulses to be inhibited as determined at block 420, the RA pacemaker 12 returns to the previously-selected, higher pacing rate at block 422. As described previously, the first two or more pulses may be delivered at a high output so that the RV pacemaker 14 can detect the change back to the higher rate and re-select the higher rate for ventricular pacing and re-establish the ventricular pacing interval phase relative to the atrial pacing interval for a desired AV delay.

If atrial pacing is sustained at the decreased atrial pacing rate, both the RA pacemaker 12 and the RV pacemaker 14 remain at the decreased rate at block 424. The RV pacemaker 14 may re-establish a desired AV delay by adjusting the phase of the VV interval relative to sensed FFAP events as needed (or the RA pacemaker 12 may re-establish the desired AV delay by adjusting the AA interval relative to sensed FFV events as needed to re-establish the desired AV delay).

In some examples, if the frequency of rate changes is low, as determined at block 430, the number of pacing rate selections may be increased at block 430. For example, if the number of pacing rates included in the limited pacing rate selection has been previously reduced at block 428, the pacing rate may be maintained at a relatively high rate for a period of time if the intrinsic rate has not dropped below the next lower rate of the reduced number of pacing rate selections. To illustrate, if the reduced selections are 65 ppm and 85 ppm and the selected rate is 85 ppm, the intrinsic rate may be at 70 bpm causing the RA device to return to 85 ppm after attempting pacing at the lower available rate of 65 ppm. The rate of changing the pacing rate may fall below an expected frequency of rate changes as determined at block 430. In this case, the RA pacemaker 12 may increase the number of pacing rate selections at block 432, e.g., back to 60, 70, 80 and 90 ppm.

If the RV pacemaker 14 has reduced the pacing rate selection, the RA pacemaker 12 may signal the RV pacemaker 14 to increase the pacing rate selection at block 432. Alternatively, RV pacemaker 14 may also detect the low frequency of pacing rate changes and automatically increase the number of pacing rate selections at block 432. As indicated above, in some cases RV pacemaker 14 does not adjust the number of pacing rate selections available when the adjusted selection of pacing rates of RA pacemaker 12 is a subset of the selection of pacing rates of RV pacemaker 14.

Figure 7:
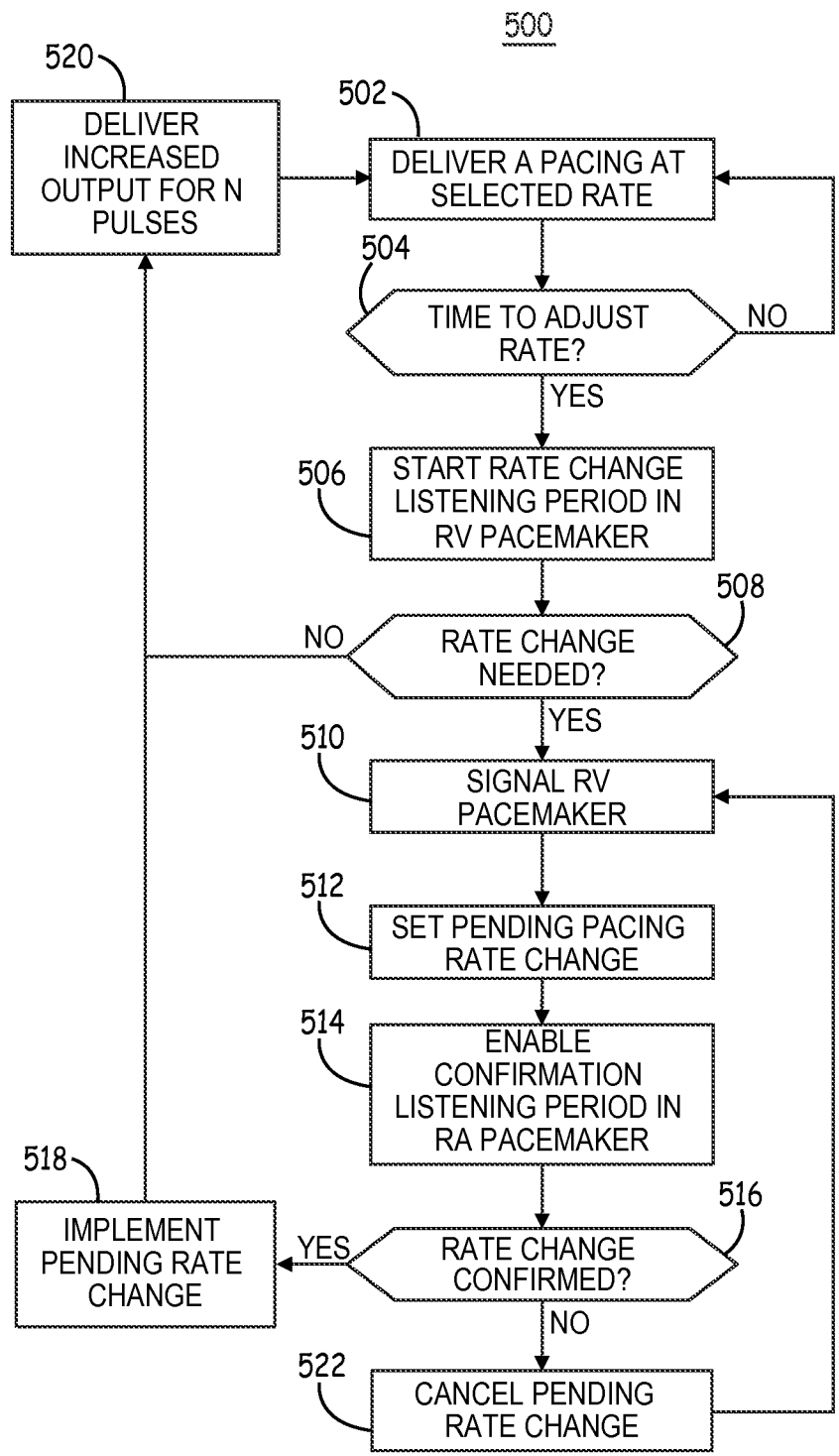
FIG. 7 is a flow chart of a method for controlling dual chamber pacing by the system of FIG. 1 according to another example.

FIG. 7 is a flow chart 500 of a method for controlling dual chamber pacing by RA pacemaker 12 and RV pacemaker 14 according to another example. At block 502, RA pacemaker 12 is operating in the AV block mode and is delivering atrial pacing pulses at a pacing rate selected from the limited pacing rate selection. At block 504, both the RA pacemaker 12 and the RV pacemaker 14 determine that it is time to adjust the pacing rate based on an expiration of a rate adjustment time interval. The rate adjustment time interval may be a fixed or adjustable time interval or a fixed or adjustable number of pacing pulses, e.g., every one minute or other predetermined time interval or number of pacing pulses. The rate adjustment time interval may be shorter when the pacing rate or SIR is at or near the high end of the limited pacing rate selections, for example, and longer when the pacing rate or SIR is at or near the low end of the limited pacing rate selections. Both control modules 206 of the respective RA pacemaker 12 and RV pacemaker 14 are configured to follow a common protocol for scheduling rate adjustment time intervals such that both pacemakers 12 and 14 reach a rate adjustment time interval expiration at approximately the same time, e.g., within approximately 10 to 100 ms of each other.

Upon expiration of the rate adjustment time interval, the RV pacemaker 14 is configured to start a rate change listening period at block 506. RV pacemaker 14 is configured to sense or receive a rate change signal from RA pacemaker 12 during the listening interval. In some examples, starting the rate change listening period is achieved by enabling FF event sensing at block 506 for the listening period, such as starting interval 365 shown in FIG. 5. FF event sensing may be enabled by increasing power to an amplifier in sensing module 202 of RV pacemaker 14. The listening period for which FF event sensing is enabled in RV pacemaker 14 may be between one and ten seconds or another predetermined time interval.

In other examples, RV pacemaker 14 starts the listening period at block 506 by enabling telemetry module 208 to listen for a wireless telemetry communication signal from RA pacemaker 12 for a predetermined time interval. In still other examples, RV pacemaker 14 may enable a sensor 212 for receiving a signal from RA pacemaker 12. For example RA pacemaker 12 may be configured to produce an acoustical alert signal that is received by an acoustical sensor included in sensors 212 of RV pacemaker 14. It is recognized that various communication modalities may be conceived that enable RV pacemaker 14 to receive a signal from RA pacemaker 12 during the listening period that is scheduled to occur at the expiration of each rate adjustment time interval. By enabling RV pacemaker 14 to detect or receive a signal from RA pacemaker 12 at scheduled rate adjustment times, power is conserved in RV pacemaker 14 by reducing how often and how long RV pacemaker 14 is required to sense or receive rate adjustment signals from RA pacemaker 12.

RA pacemaker 12 determines if a pacing rate change is needed at block 508. In some instances, the SIR may have increased and an increase in pacing rate is required. In other instances, an increase in the sensed intrinsic atrial rate, i.e., intrinsic P-waves are being sensed, requires an increase in the pacing rate. At other times, the RA pacemaker 12 may be scheduled to reduce the selected pacing rate in order to determine if a slower pacing rate is still greater than the intrinsic atrial rate (as described above in conjunction with FIG. 6). If a pacing rate increase is not required based on no increase in SIR and no increase in the rate of sensed intrinsic P-waves, the RA pacemaker 12 will attempt to decrease the pacing rate each time the rate adjustment time interval expires. In other examples, an attempt to decrease the pacing rate is made less often than every rate adjustment time interval, e.g., every other or every third rate adjustment time interval. In yet another example, an attempt at decreasing the pacing rate may be made only after a decrease in the SIR is detected.

If no rate change is needed, the RA pacemaker 12 may continue pacing at the currently selected pacing rate without signaling a rate change to the RV pacemaker 14. Even if a rate change is not needed, the RA pacemaker 12 may deliver one or more pacing pulses at an increased pacing pulse output at block 520 during the listening period. The increased atrial pacing pulse output enables RV pacemaker 14 to adjust the phase of the VV pace interval as needed relative to the AA pace interval (based on FFAP sensed events during the listening period) to maintain a desired AV delay as described above. In some examples, the increased atrial pacing pulse output may be delivered every time a rate adjustment interval expires even though a rate adjustment is not required. In other examples, the increased pacing pulse output may be delivered less often, e.g., every other listening period when two consecutive rate adjustment intervals expire without requiring a rate adjustment. The increased atrial pacing pulse output is optional, however, and may not be delivered if a rate change is not required.

If a rate adjustment is not required, the RV pacemaker 14 will not sense or receive a rate change signal. The rate adjustment listening time period started by RV pacemaker 14 at block 506 will expire. RV pacemaker 14 will disable FF event sensing by reducing power to an amplifier in sensing module 204 of RV pacemaker 14 (or by powering down telemetry module 208 or another sensor used to receive a rate change signal) and will continue delivering ventricular pacing pulses at its currently selected pacing rate. As indicated above, the RV pacemaker 14 may sense FFAP events during the listening period at block 520 for adjusting the VV pace interval phase and/or adjusting the VV interval to account for clock cycle frequency differences as described above without changing the pacing rate selection.

If RA pacemaker 12 does determine that a rate change is needed, the RA pacemaker 12 signals the rate change to RV pacemaker 14 at block 510. The signal may include one or more rate change signal pulses delivered by pulse generator 202 of RA pacemaker 12 via electrodes 162 and 164 positioned in the right atrium. The control module 206 of RA pacemaker 12 controls pulse generator 202 to deliver the rate change signal pulse(s) following a therapeutic atrial pacing pulse being delivered at the currently-selected atrial pacing rate, during the physiological refractory period of the atrium.

The FF event detector 224 of RV pacemaker 14 produces a sense event signal for each rate change signal pulse delivered by RA pacemaker 12. These sense event signals are received by control module 206 following a FFAP sense event signal within a rate change signal period, e.g., within 50 ms of the FFAP sense event signal, that corresponds to the atrial refractory period. These sense event signals are interpreted by the control module 206 of RV pacemaker 14 to determine the next ventricular pacing rate selection.

In one example, the number of rate change signal pulses sensed following a FFAP sensed event may indicate how many steps to increment or decrement the ventricular pacing rate. To illustrate, if one rate change signal is sensed by FF event detector 224 following a FFAP sensed event, RV pacemaker 14 may increase the ventricular pacing rate to the next higher rate of the available pacing rates. If two rate change signals are sensed by FF event detector 224 following a single FFAP sensed event, the RV pacemaker 14 may increase the ventricular pacing rate by two increments of the available pacing rate selection (for example from 60 ppm to 80 ppm when the rate selections include 60, 70, 80 and 90 ppm).

The decision to increment or decrement the pacing rate may be based on an amplitude and/or pulse width of the first one or more of the rate change signal pulses. For example, the first rate change signal pulse may have wide pulse width to indicate that the pacing rate selection should be increased and a relatively narrow pulse width of the first rate change signal pulse may indicate that the pacing rate selection should be decreased. The total number of rate change signal pulses indicates the total number of steps to increment or decrement the rate selection.

In other examples, coded patterns of rate change signal pulse features, including but not limited to, pulse amplitude, pulse width, inter-pulse intervals, pulse number, pulse polarity, pulse shape or any combination thereof may be stored in memory 210 of each of RA pacemaker 12 and RV pacemaker 14. A coded electrical pulse pattern is selected by RA pacemaker 12 for controlling rate change signal pulses delivered by pulse generator 202 via electrodes 162 and 164 of RA pacemaker 12 following a therapeutic atrial pacing pulse during the atrial physiological refractory period. The RV pacemaker 14 senses the rate change signal pulse(s) following a FFAP sensed event, compares the features of the rate change signal pulses to the coded patterns stored in memory 210 of RV pacemaker 14, and determines the pacing rate change from the coded pattern.

The RA pacemaker 12 sets a pending atrial pacing rate change at block 512 by selecting a different pacing rate from the limited pacing rate selection. In some examples, the RA pacemaker 12 may implement the pending rate change selection on the next cardiac cycle or other predetermined number of cardiac cycles after signaling the RV pacemaker of the rate change. It may be assumed that the RV pacemaker 14 receives the rate change signal, properly interprets the signal, and selects a new ventricular pacing rate that is equivalent to the pending atrial pacing rate. The two pacemakers 12 and 14 may be configured to implement the pending rate change immediately or after a predetermined number of pacing cycles, for example after one, two or other number of pacing cycles, after the rate change signal has been delivered by RA pacemaker 12 and presumably received by RV pacemaker 14.

In other examples, the control module 206 of RA pacemaker 12 enables a rate change confirmation listening period at block 514 after signaling the RV pacemaker 14 of the rate change. Enabling a confirmation listening period in RA pacemaker 12 may include enabling a FF event detector 224 of sensing module 204, powering up telemetry module 208 of RA pacemaker 12 to listen for a return or confirmation ping from RV pacemaker 14 or enabling another sensor in sensors 212 of RA pacemaker 12 to receive a signal from RV pacemaker 14 that confirms that RV pacemaker 14 has successfully received the rate change signal and/or successfully changed the ventricular pacing rate to a rate equivalent to the new atrial pacing rate selection.

It is contemplated that confirmation of a pending or implemented rate change may be performed according to numerous techniques. For example, the pending rate change may be implemented by RA pacemaker 12, and control module 206 of RA pacemaker 12 may confirm that FFV sensed event signals (which may correspond to ventricular pacing pulses or evoked R-waves) follow delivered atrial pacing pulses in a 1:1 ratio and/or at an expected AV delay. In this case, enabling the confirmation listening period in RA pacemaker 12 at block 514 may include enabling the FF event detector 224 to sense FFV events, e.g., by increasing power to a FF event detector amplifier.

In other examples, RV pacemaker 14 may be configured to transmit a confirmation ping from telemetry module 208 to the telemetry module 208 of RA pacemaker 12. In still other examples, RA pacemaker 12 may power a sensor 212 to receive a signal indicative of a ventricular rate change, e.g., a heart sound following an atrial pacing pulse. In some cases, RV pacemaker 14 does not need to actively produce a confirmation signal but merely implement the pending rate change so that RA pacemaker 12 can sense or detect far field ventricular signals (electrical or mechanical) that are indicative of the rate change. In other examples, RV pacemaker 14 may actively produce a rate change confirmation signal such as a wireless RF telemetry signal.

In another example of actively producing a rate change confirmation signal, control module 206 of RV pacemaker 14 may be configured to control pulse generator 202 to deliver one or more electrical pulses via electrodes 162 and 164 positioned in the ventricle during the ventricular physiological refractory period following a ventricular pacing pulse as a rate change confirmation signal to RA pacemaker 12. A single pulse sensed by FF event detector 224 of RA pacemaker 12 after producing a FFV sensed event signal (corresponding to a therapeutic pacing pulse delivered at a selected pacing rate) may be a rate change confirmation signal. In other examples, the RV pacemaker 14 may be configured to control pulse generator 202 to echo the same coded pulse pattern back to RA pacemaker 12 during the physiological ventricular refractory period as was received from RA pacemaker 12 during the rate change listening period.

If the pending rate change of RV pacemaker 14 is confirmed by RA pacemaker 12 at block 516, based on signals sensed or received during the confirmation listening period, the pending rate change is confirmed at block 518. RA pacemaker 12 adopts the rate change at block 518 if it has not already been implemented. The two pacemakers 12 and 14 may be configured to adopt the confirmed rate change at block 518 at a predetermined number of pacing pulses or cycles after the rate change signal is delivered/received or after the confirmation signal is delivered/received. In other examples, the rate change is implemented at block 512 by RA pacemaker 12 upon setting the pending change and FF signals are used to confirm that RV pacemaker 14 has also implemented an equivalent rate change, in which case the pending change is confirmed at block 518 by allowing the rate change to remain in effect.

Increased atrial pacing pulse output may be delivered in conjunction with the rate change signal at block 520 for facilitating adjustment of the VV pace interval relative to the AA pace interval as described previously herein.

If the RA pacemaker 12 does not sense or receive a rate change confirmation signal at block 516, the RA pacemaker 12 may cancel the pending rate change at block 522. If the atrial rate has already been adjusted when the pending rate change was set at block 512 to enable sensing for an equivalent ventricular rate change during the confirmation listening period, the atrial pacing rate may be set back to the previously selected pacing rate at block 522 if the equivalent ventricular rate change is not confirmed during the confirmation listening period. If the atrial rate change is pending but not yet implemented during the confirmation listening period, the pending change may be cancelled at block 522 without ever implementing the change.

If the pending rate change is cancelled at block 522, the RA pacemaker 12 may resend the rate change signal at block 510. In some cases, the RV pacemaker 14 is configured to set the rate change listening period to a time interval that is long enough to allow RA pacemaker to send the rate change signal, set a confirmation listening period to confirm, and resend a second rate change signal if the rate change is not confirmed. In other examples, the RA pacemaker 12 may return to block 502 to continue pacing at the previously selected rate and wait for the next rate change adjustment interval to expire to resend a rate change signal.

Figure 8:
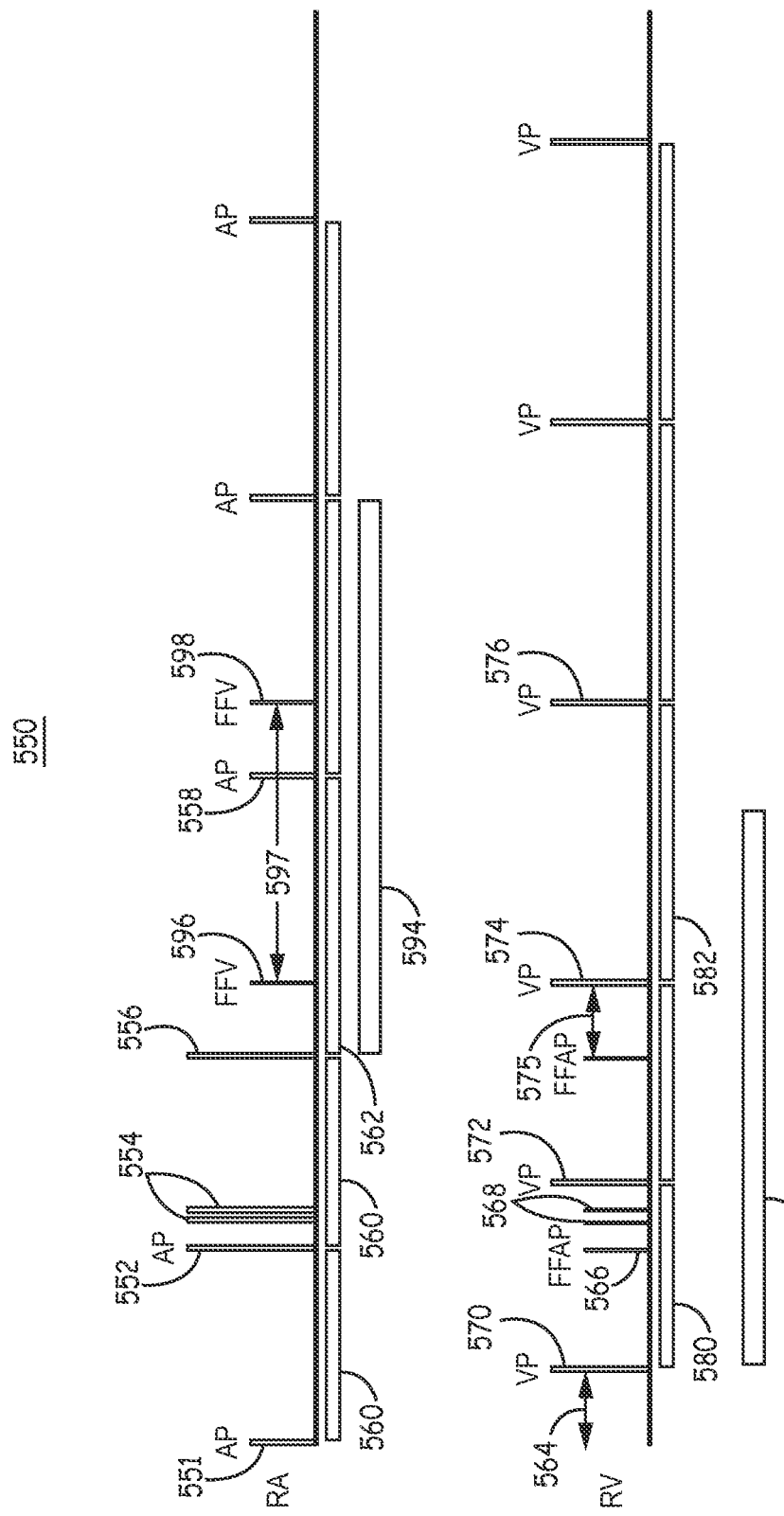
FIG. 8 is a timing diagram of pacing pulses delivered by the system of FIG. 1 according to another example.

FIG. 8 is a timing diagram 550 of RA pacing pulses delivered by RA pacemaker 12 and RV pacing pulses delivered by RV pacemaker 14. RA pacing pulse (AP) 551 represents the last atrial pacing pulse upon expiration of a rate adjustment time interval. RV pacing pulse (VP) 570 represents the last ventricular pacing pulse upon expiration of the rate adjustment interval. RV pacemaker 14 sets a rate change listening period 590.

The RA pacemaker 12 determines, in this example, that a rate change is needed to decrease the pacing rate. The next atrial pacing pulse 552 is delivered at a high pacing output, still at an AA pace interval 560 corresponding to the currently-selected, unadjusted atrial pacing rate. The pulse generator 202 of RA pacemaker 12 is controlled to deliver one or more coded signal pulses 554 during the atrial physiological refractory period following atrial pacing pulse 552. The rate change signal pulses 554 may be coded for the number of rate increments that should be made or for the specific rate selection that should be made. In the example shown, two signal pulses 554 may indicate increment the rate by two steps, e.g., from 60 ppm to 80 ppm when the limited rate selection includes 10 ppm increments.

Alternatively, the rate change signal pulses 554 may include a feature or pattern of pulse amplitude, pulse width, inter-pulse interval, and/or pulse number that is stored as a coded pattern for a specific rate selection e.g., 80 ppm. In this case, whatever the currently selected rate is (greater than or less than 80 ppm), 80 ppm is selected as the pending rate by RV pacemaker 14 in response to rate change signal 554.

During rate change listening period 590, RV pacemaker 14 senses the FFAP event 566 corresponding to the high output atrial pacing pulse 552 and then senses the far field rate change signals 568 corresponding to rate change signal pulses 554. RV pacemaker 14 delivers the next ventricular pacing pulse 572 at the currently selected ventricular pacing rate upon expiration of VV pace interval 580 (equivalent to AA pace interval 560 but shifted in phase to result in a desired AV delay 564).

On the next atrial pacing pulse 556 after sending the rate change signal pulses 554, an increased AA pace interval 562 is started corresponding to the decreased pacing rate selected from the limited pacing rate selection. RA pacemaker 12 may start a confirmation listening period 594 after delivering atrial pacing pulse 556 for verifying that RV pacemaker 14 has received the rate change signal and/or implemented the rate change. In other examples, confirmation listening period may be started upon producing rate change signal pulses 554 to wait for confirmation signal from RV pacemaker 14.

The RV pacemaker 14 delivers one more ventricular pacing pulse 574 at the same, currently selected pacing rate interval 580 to complete one pacing cycle (AP 556 and VP 574) after rate change signal 554 was produced. A VV pace interval 582 corresponding to the new, decreased rate is started upon ventricular pacing pulse 574 such that the switch to the new pacing rate occurs simultaneously by RA pacemaker 12 and RV pacemaker 14 on the same pacing cycle. RV pacemaker 14 may use sensed FFAP events 566 during rate change listening period 590 for adjusting the phase of VV interval 582 for establishing a desired AV interval 575 as described previously.

RA pacemaker 12 may start the confirmation listening period 594 in order to enable FFV event sensing to confirm that RV pacemaker 14 has implemented the expected rate change. FFV sensed events 596 and 598 may be sensed and the FFV time interval 597 may be determined and compared to the AA pace interval 562. One or more FFV time intervals may be required for confirming the ventricular pacing rate change and confirmation listening period 594 may be set accordingly.

If the ventricular pacing rate change is confirmed during confirmation listening period 594, the pacing continues at the new rate in both the atrial and ventricular chambers as shown in FIG. 8. If the correct ventricular pacing rate change is not confirmed by RA pacemaker 12, RA pacemaker 12 may revert back to the previously selected pacing rate interval 560 and wait for the next rate adjustment interval to expire to resend a rate change signal if still needed. In other examples, rate change listening period 590 may be set to expire one or more pacing cycles after confirmation listening period 594 (or one or more rate change and listing confirmation periods may be repeated) to allow RA pacemaker 12 to attempt resending the rate change signal pulses 554 during the same rate change listening period 590.

In the example shown, rate change signal 554 includes two electrical pulses generated by pulse generator 202 of RA pacemaker 12. In other examples, the rate change signal may be a wireless RF signal or an acoustic ping instead of the electrical pulses shown here. The wireless RF signal or acoustic ping is received by RV pacemaker 14 (via telemetry module 208 or sensors 212) during the rate change listening period 590. Similarly, RV pacemaker 14 may produce a confirmation signal that is an RF telemetry signal transmitted by telemetry module 208 or an acoustic ping produced by sensors 212 during confirmation listening period 594 (which may be started earlier after rate change signal 554).

In the examples presented herein, it is generally presumed that the RA pacemaker 12 is configured to determine the needed pacing rate, selecting the rate from the limited pacing rate selection, and signaling the RV pacemaker 14 to establish ventricular pacing rate that is equivalent to the selected atrial pacing rate. It is contemplated however, that the RV pacemaker 14 may determine a need to adjust the pacing rate at least some of the time, e.g., based on a SIR determined by the RV pacemaker 14, and signal the RA pacemaker 12 of a selected pacing rate using any of the techniques disclosed herein, including setting a rate change listening period in the RA pacemaker 12, producing a rate change signal by the RV pacemaker 14, and optionally setting a confirmation listening period in the RV pacemaker 14.

In some examples, both the RA pacemaker 12 and the RV pacemaker 14 may be configured to initiate a rate change, which may be initiated only upon expiration of rate change time intervals. Two different rate change time intervals may be set, e.g., in a staggered manner, in each pacemaker 12 and 14. RA pacemaker 12 generates the rate change signal (if needed) and RV pacemaker 14 listens for the signal at the expiration of one rate change time interval expiration. RV pacemaker 14 generates the rate change signal (if needed), and the RA pacemaker 12 listens for the signal at the expiration of the other rate change time interval.

Figure 9:
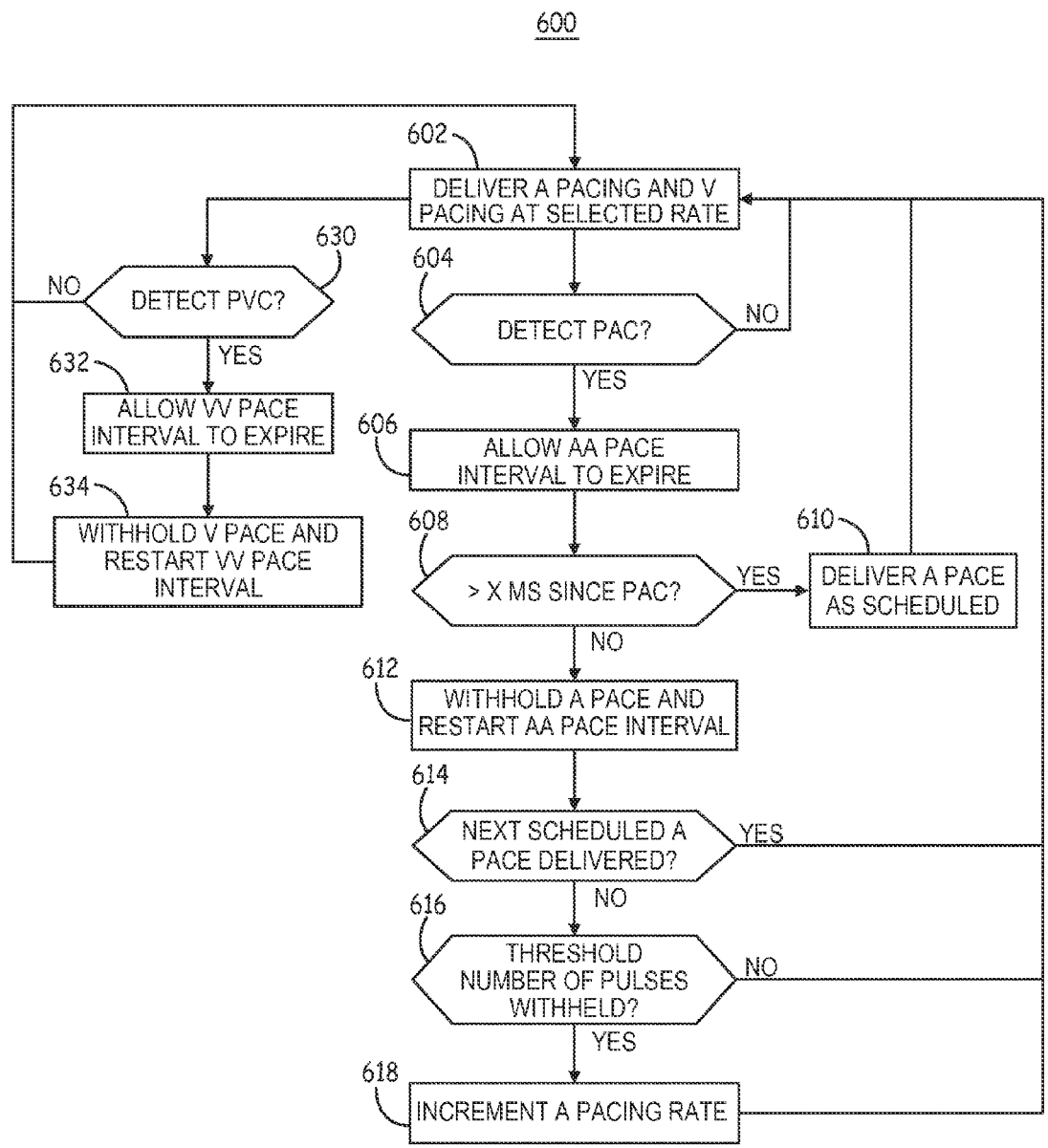
FIG. 9 is a flow chart of a method for controlling dual chamber pacing delivered by the system of FIG. 1 in the presence of premature contractions.

FIG. 9 is a flow chart 600 of a method for controlling dual chamber pacing delivered by RA pacemaker 12 and RV pacemaker 14 in the presence of premature contractions. In some patients, premature contractions may occur during the AV block pacing mode when atrial and ventricular pacing is being delivered at the selected, equivalent pacing rates by the separate RA and RV pacemakers 12 and 14 at block 602.

If a premature atrial contraction (PAC) is detected at block 604 (during the AV block pacing mode), the AA pace interval started on the preceding atrial pacing pulse is allowed to expire at block 606. The scheduled atrial pacing pulse may be withheld, and a new AA pace interval is restarted to schedule the next atrial pacing pulse at block 612. In some examples, if adequate time has elapsed since the detected PAC when the AA pace interval expires, as determined at block 608, the scheduled atrial pacing pulse may be delivered as scheduled at block 610. For example, if at least 500 ms have expired since the PAC detection at block 604 when the AA pace interval expires, the atrial pacing pulse is delivered and pacing continues at the selected rate at block 602.

If the scheduled atrial pacing pulse is withheld at block 612, the next AA pace interval is started to schedule the next atrial pacing pulse. If the next atrial pacing pulse is delivered as scheduled, pacing continues at the selected rate. In some instances, another sensed P-wave may occur during the next AA pace interval causing the next scheduled atrial pacing pulse to also be withheld. If the next scheduled pacing pulse is not delivered as determined at block 614, the RA pacemaker 12 may continue allowing the AA pacing escape intervals to expire and withhold atrial pacing pulses as needed until an AA pacing escape interval expires without a sensed atrial P-wave causing inhibition of the atrial pacing pulse. Eventually an atrial pacing pulse will be delivered, and the control module 206 of RA pacemaker 12 will have maintained the AA pace interval running on schedule according to the selected pacing rate.

In another example, if a threshold number of pulses have been withheld (which may be one or more pacing pulses) as determined at block 616, the atrial pacing rate may be increased to the next higher rate of the limited pacing rate selection at block 618 in order to regain pacing control of the atrial rate. The rate increase may occur upon expiration of a rate adjustment time interval so that the RA pacemaker 12 can signal the RV pacemaker 14 of the rate adjustment using any of the methods described above in conjunction with FIGS. 7 and 8. The number of sensed P-waves allowed to occur before increasing the atrial pacing rate is limited in order to overdrive pace the intrinsic rate, thereby maintaining pacing control of the atrial rate and avoiding an intrinsic atrial rate that is asynchronous with the paced ventricular rate. If the sensed atrial rate is greater than a tachyarrhythmia detection rate (or greater than the highest available rate of the limited selection of pacing rates), however, atrial pacing is inhibited and the RV pacemaker 14 may pace at the ventricular SIR determined by control module 206 of RV pacemaker 14.

If a premature ventricular contraction (PVC) is detected by RV pacemaker 14 at block 630 during the AV block pacing mode, the VV pace interval is allowed to expire at block 632. The scheduled ventricular pacing pulse is withheld at block 634 and the VV pace interval is restarted. Since AV block is present, it is expected that the next VV pace interval will expire without a sensed R-wave such that ventricular pacing at the selected pacing rate is quickly regained. If an additional ventricular pacing pulse is inhibited due to another PVC, the VV pacing escape interval continues to be allowed to expire and restarted on schedule according to the selected pacing rate until a ventricular pacing pulse is eventually delivered and pacing control is regained. If R-wave sensing returns, however, resulting in inhibited ventricular pacing pulses, the RV pacemaker 14 may detect a return of AV conduction. RA pacemaker 12 and RV pacemaker 14 may switch back to an AV conduction mode of pacing in which the RA pacemaker 12 returns to full pacing rate selection and RV pacemaker 14 returns to backup ventricular pacing as described previously.

Figure 10:
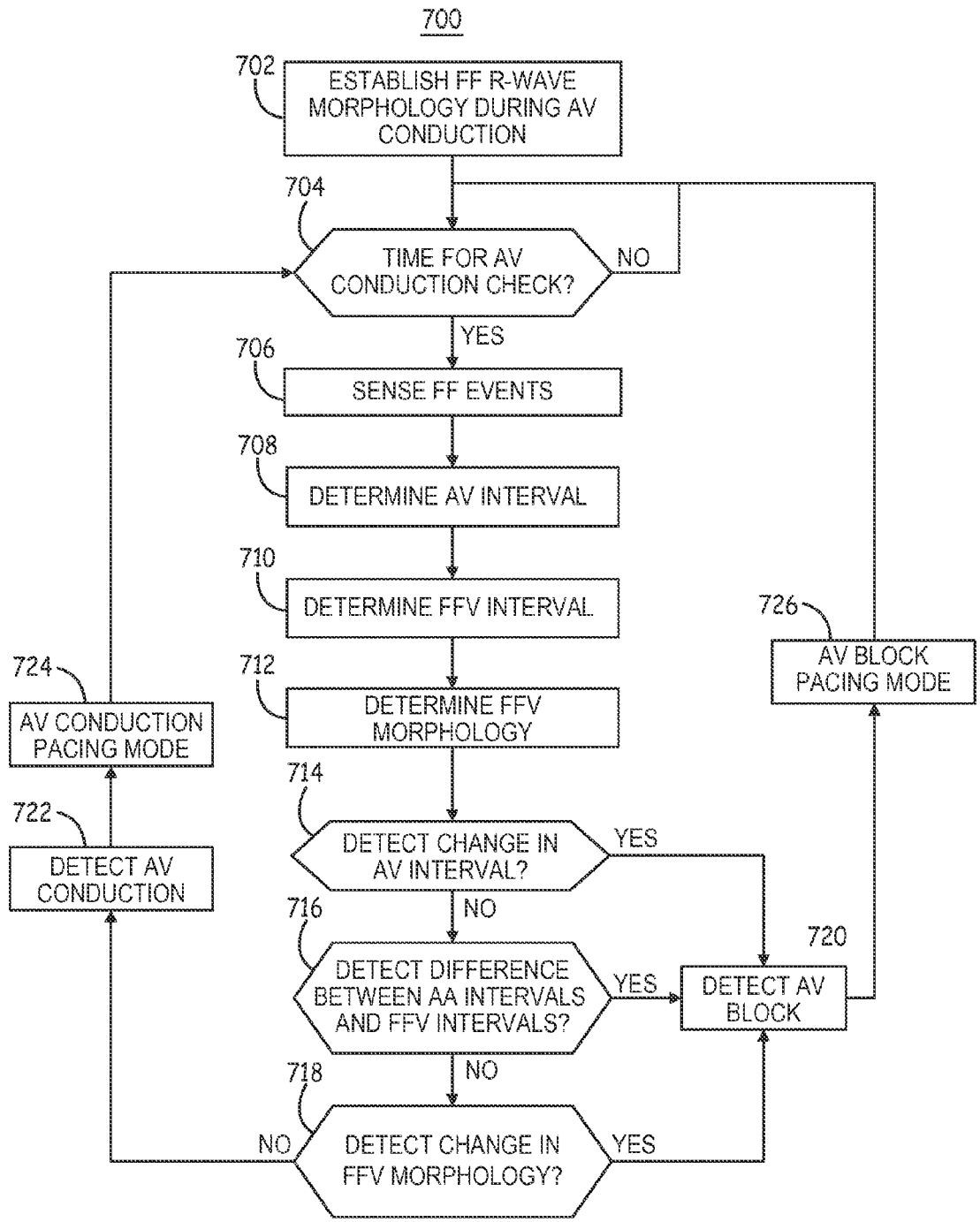
FIG. 10 is a flow chart of a method for detecting AV block by the atrial pacemaker of FIG. 1.

FIG. 10 is a flow chart of a method for detecting AV block by RA pacemaker 12 according to one example. At block 702, a FF R-wave morphology template or feature may be established during known AV conduction. Sensing module 202 may pass an atrial EGM signal to control module 206 of RA pacemaker 12 for analysis and generation of a FF R-wave morphology template of the overall FF R-wave shape and/or one or more FF R-wave features such as amplitude, signal width, polarity, slope or other features.

At block 704, the control module 206 of RA pacemaker 12 determines if it is time for an AV conduction check. AV conduction checks may be performed on a scheduled basis during the AV block pacing mode to determine if AV conduction has returned. Both RA pacemaker 12 and RV pacemaker 14 may be configured to perform simultaneous AV conduction checks to promote synchronized switching between AV block and AV conduction pacing modes of the two pacemakers 12 and 14. During AV conduction, RA pacemaker 12 may be configured to monitor for AV block beat-by-beat or on a less frequent schedule, e.g. once per minute, once per hour, once per day or other schedule which may be tailored to the patient. Power may be conserved by enabling FF event detector 224 to sense FF ventricular events only on a scheduled basis instead of beat-by-beat.

At block 706 FF event detector 224 of RA pacemaker 12 is enabled for sensing FF ventricular events. A sensed FF ventricular event may be used for determining an AV interval at block 708 (between a paced or sensed atrial event and the subsequently sensed FF ventricular event), determine FF event interval at block 710 between two consecutive FF sensed events, and/or the FF sensed event morphology. A change in AV interval, FFV event interval, FFV morphology or any combination thereof may lead to detection of AV block at block 720 based on the analyses performed at blocks 714, 716 and 718.

At block 714, the control module 206 may compare the AV interval to a previously determined AV interval to determine if the AV interval has changed substantially, indicating asynchrony between the atrium and the ventricle as evidence of AV block. In some examples, the atrial pacing rate may be varied during the AV conduction block check to determine if the AV interval stays within an expected range consistent with AV conduction or if the AV interval changes as the atrial pacing rate changes. A method for detecting AV block that includes altering the atrial pacing rate and monitoring the AV interval is generally disclosed in the above-incorporated U.S. patent application Ser. No. 14/227,962).

At block 716, one or more FFV intervals determined at block 710 may be compared to sensed or paced AA intervals of the same respective cardiac cycles. If the FFV intervals are longer or shorter than the corresponding AA intervals by more than a threshold range, AV block is indicated.

A sensed FF event morphology may be compared to the previously established FF R-wave morphology during known AV conduction. A morphology matching score of correlation between a sensed FFV waveform and the stored FF R-wave morphology may be determined, e.g., using a wavelet transform analysis, or individual morphology features may be compared, e.g., peak amplitude, polarity, slope, width etc. If a significant change in the FFV morphology is detected, this change may be evidence that the FFV is not an R-wave arising from a depolarization conducted normally via the AV node.

If a change in the AV interval, a difference between the AA and FFV intervals, and/or a change in the FFV morphology is detected, AV block is detected at block 720. In response to the AV block detection, RA pacemaker 12 will switch to or remain in the AV block pacing mode using a limited pacing rate selection.

If the RA pacemaker 12 is operating in the AV conduction mode and pacing the atrium or inhibiting pacing such that the atrial intrinsic activity is driving the heart rate, an AV interval that is consistently within a range of a physiological AV interval and a FFV interval that is approximately equal to the AA interval is evidence of intact AV conduction. The ventricular rate is following the atrial paced or sensed rate. AV conduction may be detected at block 722 based on the expected AV interval(s) and/or FFV interval(s). In some examples, the FFV morphology may be confirmed to match the previously established FF R-wave morphology at block 718 for detecting AV conduction at block 722. The RA pacemaker 12 will continue the AV conduction mode of pacing at block 724.

The RA pacemaker 12 may be operating in the AV block pacing mode during the AV conduction test so that it is pacing at a selected one of the limited selection of pacing rates. In this case, if the AV interval(s) determined at block 708 have not changed, i.e., they are maintained at a desired target AV delay, as determined at block 714, and the FFV interval is approximately equal to the AA interval as determined at block 716, either the RV pacemaker 14 is pacing the ventricle synchronously with the atrial pacing at the desired AV delay or AV conduction has returned. In order to verify that AV conduction has returned, the control module 206 of RA pacemaker 12 may compare the FFV morphology to the previously established FF R-wave morphology at block 718.

If the FFV morphology matches the known conducted R-wave morphology, AV conduction is detected at block 722. The RA pacemaker 12 switches to the AV conduction pacing mode at block 724 by enabling pacing at the full pacing rate selection. If the FFV morphology does not match the known conducted R-wave morphology at block 718, AV block is detected. The RA pacemaker 12 remains in the AV block pacing mode at block 726.

In some instances, the RA pacemaker 12 and the RV pacemaker 14 may be configured to test for AV conduction at the same scheduled time during the AV block pacing mode such that the RV pacemaker 14 will extend a VV pacing interval in order to allow the RA pacemaker 12 to detect a change in the AV interval or difference between the AA and FFV intervals at blocks 714 and 716, respectively, resulting in AV block detection at block 720 without checking the FFV morphology at block 718.

Accordingly, in various examples, one or more of the criteria relating to AV interval, FFV interval changes relative to AA intervals and change in FFV morphology may be used for detecting AV block and for detecting AV conduction. The criteria used may vary between embodiments and may depend on which pacing mode the pacemakers 12 and 14 are operating in at the time of the conduction check. The blocks shown in FIG. 10 and in other flow charts presented herein may be performed in a different order or different combination than the specific order and combination described here.

Thus, various examples of an implantable medical device system for delivering coordinated atrial and ventricular pacing using separate intracardiac pacemakers have been described according to illustrative embodiments. However, various modifications may be made to the described embodiments without departing from the scope of the following claims.

The invention claimed is:

1. A method for controlling cardiac pacing by an implantable medical device system comprising a first chamber pacemaker and a second chamber pacemaker, the method comprising:
   selecting by a control module of the first chamber pacemaker a first chamber pacing rate from a first plurality of selectable pacing rates;
   automatically detecting atrioventricular (AV) block;
   in response to detecting the AV block, establishing a second plurality of selectable pacing rates comprising fewer selectable pacing rates than the first plurality of selectable pacing rates;
   selecting a first rate from the second plurality of selectable pacing rates;
   adjusting the first chamber pacing rate to the first rate;
   delivering first pacing pulses to a first heart chamber at the selected first rate;
   establishing a second chamber pacing rate that is equivalent to the first rate in response to detecting the AV block; and
   delivering second pacing pulses to a second heart chamber at the second chamber pacing rate.

2. The method of claim 1, further comprising:
   establishing a third plurality of selectable pacing rates by the second chamber pacemaker in response to detecting the AV block, wherein the third plurality of selectable pacing rates is equivalent to the second plurality of selectable pacing rates;
   wherein selecting the first rate comprises determining by the first chamber pacemaker a first sensor indicated pacing rate and selecting the first rate to be greater than the first sensor indicated pacing rate; and
   wherein establishing the second chamber pacing rate equivalent to the first rate comprises determining by the second chamber pacemaker a second sensor indicated pacing rate and selecting the first rate from the third plurality of pacing rate selections to be greater than the second sensor indicated pacing rate.

3. The method of claim 1, wherein selecting the first rate comprises:
   determining a first chamber intrinsic heart rate;
   determining a first sensor indicated pacing rate; and
   selecting the first rate to be greater than a higher one of the first chamber intrinsic heart rate and the first sensor indicated pacing rate.

4. The method of claim 1, further comprising:
   delivering a first portion of the first pacing pulses at the first rate and a first pulse output;
   delivering a second portion of the first pacing pulses at the first rate and a second pulse output less than the first pulse output;
   sensing the first portion of the first pacing pulses by the second chamber pacemaker;
   determining the first rate from the sensed first portion of the first pacing pulses; and
   establishing the second chamber pacing rate to be equivalent to the determined first rate.

5. The method of claim 4, further comprising:
   delivering a first portion of the first pacing pulses at the first rate and a first pulse output;
   delivering a second portion of the first pacing pulses at the first rate and a second pulse output less than the first pulse output;
   sensing the first portion of the first pacing pulses by the second chamber pacemaker;
   determining a first chamber pacing interval from the sensed first portion of the first pacing pulses; and
   determining a difference in a first chamber pacemaker clock cycle frequency and a second chamber pacemaker clock cycle frequency in response to the determined first chamber pacing interval;
   setting a second chamber pace interval corresponding to the established second chamber pacing rate; and
   adjusting the second chamber pace interval by the determined difference.

6. The method of claim 1, further comprising:
   delivering a first portion of the first pacing pulses at the first rate and a first pulse output;
   delivering a second portion of the first pacing pulses at the first rate and a second pulse output less than the first pulse output;
   sensing the first portion of the first pacing pulses by the second chamber pacemaker; and
   establishing a phase of a second chamber pace interval of the first rate in response to the sensed first portion of the first pacing pulses.

7. The method of claim 1, further comprising:
   determining a need to adjust the first chamber pacing rate from the first rate;
   selecting a second rate from the second plurality of selectable pacing rates;
   adjusting the first chamber pacing rate to the selected second rate; and
   delivering third pacing pulses to the first heart chamber at the second rate.

8. The method of claim 7, further comprising:
   scheduling a rate change interval;
   adjusting the first chamber pacing rate to the selected second rate after the expiration of the rate change interval.

9. The method of claim 8, further comprising:
   scheduling a rate change listening period by the second chamber pacemaker upon expiration of the rate change interval;
   producing a rate change signal by the first chamber pacemaker after the expiration of the rate change interval;
   detecting the rate change signal by the second chamber pacemaker during the rate change listening period;
   determining the second rate by the second chamber pacemaker in response to the detected rate change signal;
   adjusting the second chamber pacing rate to the determined second rate; and
   delivering fourth pacing pulses to the second heart chamber at the second rate.

10. The method of claim 7, further comprising:
    storing an electrical pulse code in a memory of each of the first chamber pacemaker and the second chamber pacemaker;
    generating by the first chamber pacemaker at least one electrical pulse during a first chamber physiological refractory period to signal the selected second rate to the second chamber pacemaker according the electrical pulse code;
    sensing the at least one electrical pulse;
    determining the second rate by the second chamber pacemaker based on the sensed at least one electrical pulse and the stored electrical pulse code; and
    adjusting the second chamber pacing rate to the determined second rate.

11. The method of claim 1, further comprising:
selecting different ones of the second plurality of pacing rates in response to changes in at least one of a sensed intrinsic rate and a sensor indicated pacing rate;
determining a frequency of selecting the different ones of the second plurality of pacing rates;
comparing the frequency to a change threshold; and
in response to the frequency meeting the change threshold, adjusting the second plurality of selectable pacing rates to a third plurality of selectable pacing rates, the third plurality of selectable pacing rates comprising a different number of selectable pacing rates than the second plurality of selectable pacing rates and the first plurality of selectable pacing rates.

12. An implantable medical device system, comprising:
a first chamber pacemaker comprising a first pacing pulse generator, a first sensing module and a first control module coupled to the first pacing pulse generator and the first sensing module; and
a second chamber pacemaker comprising a second pacing pulse generator, a second sensing module, and a second control module coupled to the second pulse generator and the second sensing module,
the first chamber pacemaker configured to:
select a first chamber pacing rate from a first plurality of selectable pacing rates;
detect atrioventricular (AV) block;
in response to detecting the AV block, establish a second plurality of selectable pacing rates comprising fewer selectable rates than the first plurality of selectable pacing rates;
select a first rate from the second plurality of selectable pacing rates;
adjust the first chamber pacing rate to the first rate; and
control the first chamber pulse generator to deliver first pacing pulses to a first heart chamber at the selected first rate;
the second control module configured to:
detect the AV block;
establish a second chamber pacing rate that is equivalent to the first rate in response to detecting the AV block; and
control the second pacing pulse generator to deliver second pacing pulses to a second heart chamber at the second chamber pacing rate.

13. The system of claim 12, wherein the first chamber pacemaker comprises a first sensor and the second chamber pacemaker comprises a second sensor, wherein:
the first control module is configured to select the first rate by determining a first sensor indicated pacing rate based on a signal from the first sensor and select the first rate to be greater than the first sensor indicated pacing rate; and
the second control module is configured to:
establish a third plurality of pacing rate selections in response to detecting AV block, the third plurality of pacing rate selections equivalent to the second plurality of pacing rate selections, and
establish the second chamber pacing rate equivalent to the first rate by determining a second sensor indicated pacing rate based on a signal from the second sensor and select the first rate from the third plurality of pacing rate selections, the selected first rate greater than the second sensor indicated pacing rate.

14. The system of claim 12, wherein:
the first chamber pacemaker comprises a rate response sensor;
the first chamber pacemaker configured to select the first rate by:
determining a first chamber intrinsic heart rate from signals received from the first sensing module;
determining a sensor indicated pacing rate in response to a signal from the rate response sensor; and
select the first rate to be greater than a higher one of the first chamber intrinsic heart rate and the sensor indicated pacing rate.

15. The system of claim 12, wherein:
the first control module is configured to:
control the first pulse generator to deliver a first portion of the first pacing pulses at the first rate and a first pulse output; and
control the first pulse generator to deliver a second portion of the first pacing pulses at the first rate and a second pulse output less than the first pulse output; and
the second control module is configured to:
control the second sensing module to sense the first portion of the first pacing pulses;
determine the first rate from the sensed first portion of the first pacing pulses; and
establish the second chamber pacing rate to be equivalent to the determined first rate.

16. The system of claim 15, wherein:
the first control module is configured to:
control the first pulse generator to deliver a first portion of the first pacing pulses at the first rate and a first pulse output;
control the first pulse generator to deliver a second portion of the first pacing pulses at the first rate and a second pulse output less than the first pulse output;
the second control module is configured to:
control the second sensing module to sense the first portion of the first pacing pulses;
determine a first pacing interval from the sensed first portion of the first pacing pulses; and
determine a difference in a first clock cycle frequency of the first pacemaker and a second clock cycle frequency of the second pacemaker in response to the determined first pacing interval;
set a second pace interval corresponding to the established second chamber pacing rate; and
adjust the second pace interval by the determined difference.

17. The system of claim 12, wherein:
the first control module is further configured to:
control the first pulse generator to deliver a first portion of the first pacing pulses at the first rate and a first pulse output;
deliver a second portion of the first pacing pulses at the first rate and a second pulse output less than the first pulse output;
the second control module is further configured to:
control the second sensing module to sense the first portion of the first pacing pulses; and
establish a phase of a second chamber pace interval of the first rate in response to the sensed first portion of the first pacing pulses.

18. The system of claim 12, wherein the first control module is further configured to:
determine a need to adjust the first chamber pacing rate from the first rate;
select a second rate from the second plurality of selectable pacing rates;

adjust the first chamber pacing rate to the selected second rate; and control the first pulse generator to deliver third pacing pulses to the first heart chamber at the second rate.

19. The system of claim 18, wherein the first control module is further configured to:
schedule a rate change interval;
adjust the first chamber pacing rate to the selected second rate after the expiration of the rate change interval.

20. The system of claim 19, wherein:
the first chamber pacemaker is configured to:
generate a rate change signal after the expiration of the rate change interval;
the second control module is configured to:
schedule a rate change listening period upon expiration of the rate change interval;
detect the rate change signal during the rate change listening period;
determine the second rate in response to the detected rate change signal;
adjust the second chamber pacing rate to the determined second rate; and
control the second pulse generator to deliver fourth pacing pulses to the second heart chamber at the second rate.

21. The system of claim 18, wherein:
each of the first chamber pacemaker and the second chamber pacemaker comprise a memory storing an electrical pulse code;
the first control module is configured to control the first pulse generator to generate at least one electrical pulse during a first chamber physiological refractory period to signal the selected second rate to the second chamber pacemaker according the electrical pulse code;
the second control module is configured to:
control the second sensing module to sense the at least one electrical pulse;
determine the second rate based on the sensed at least one electrical pulse and the stored electrical pulse code; and
adjust the second chamber pacing rate to the determined second rate.

22. The system of claim 12, wherein the first control module is further configured to:
select different ones of the second plurality of pacing rates in response to changes in at least one of a sensed intrinsic rate and a sensor indicated pacing rate;
determine a frequency of selecting the different ones of the second plurality of pacing rates;
compare the frequency to a change threshold; and
in response to the frequency meeting the change threshold, adjust the second plurality of selectable pacing rates to a third plurality of selectable pacing rates, the third plurality of selectable pacing rates comprising a different number of selectable pacing rates than the second plurality of selectable pacing rates and the first plurality of selectable pacing rates.

23. A non-transitory, computer-readable medium comprising a set of instructions which, when executed by an implantable medical device system comprising a first chamber pacemaker and a second chamber pacemaker, cause the system to:
select a first chamber pacing rate from a first plurality of selectable pacing rates;
detect atrioventricular (AV) block;
in response to detecting the AV block, establish a second plurality of selectable pacing rates comprising fewer selectable pacing rates than the first plurality of selectable pacing rates;
select a rate from the second plurality of selectable pacing rates;
adjust the first chamber pacing rate to the selected rate;
deliver first pacing pulses to a first heart chamber at the selected rate;
establish a second chamber pacing rate that is equivalent to the selected rate in response to detecting the AV block; and
deliver second pacing pulses to a second heart chamber at the second chamber pacing rate.

* * * * *